United States Patent [19]

Pompei

[11] Patent Number: 5,445,158
[45] Date of Patent: * Aug. 29, 1995

[54] RADIATION DETECTOR PROBE

[75] Inventor: Francesco Pompei, Boston, Mass.

[73] Assignee: Exergen Corporation, Newton, Mass.

[ * ] Notice: The portion of the term of this patent subsequent to Feb. 19, 2008 has been disclaimed.

[21] Appl. No.: 760,006

[22] Filed: Sep. 13, 1991

Related U.S. Application Data

[60] Continuation-in-part of Ser. No. 646,855, Jan. 28, 1991, Pat. No. 5,199,436, which is a division of Ser. No. 338,968, Apr. 14, 1989, Pat. No. 5,012,813, which is a continuation-in-part of Ser. No. 280,546, Dec. 6, 1988, Pat. No. 4,993,419.

[51] Int. Cl.$^6$ ............................................. A61B 6/00
[52] U.S. Cl. .................................... 128/664; 128/736
[58] Field of Search .............. 128/664, 736; 374/123, 374/127, 129, 132–133, 135

[56] References Cited

U.S. PATENT DOCUMENTS

| | | |
|---|---|---|
| 2,658,390 | 11/1953 | Machler . |
| 2,984,747 | 5/1991 | Walker ........................ 250/83.3 |
| 3,282,106 | 11/1966 | Barnes . |
| 3,491,596 | 1/1970 | Dean . |
| 3,581,570 | 6/1971 | Wortz . |
| 3,878,836 | 4/1975 | Twentier . |
| 3,949,740 | 4/1976 | Twentier . |
| 4,005,605 | 2/1977 | Michael . |
| 4,062,239 | 12/1977 | Fowler et al. . |
| 4,372,690 | 2/1983 | Berman et al. ........................ 374/29 |
| 4,456,390 | 6/1984 | Junkert et al. . |
| 4,566,808 | 1/1986 | Pompei et al. . |
| 4,602,642 | 7/1986 | O'Hara et al. . |
| 4,614,442 | 9/1986 | Poncy . |
| 4,626,686 | 12/1986 | Pompei et al. . |
| 4,634,294 | 1/1987 | Christol et al. . |
| 4,636,091 | 1/1987 | Pompei et al. . |
| 4,662,360 | 5/1987 | O'Hara et al. . |
| 4,684,018 | 8/1987 | Jarund . |
| 4,722,612 | 2/1988 | Junkert et al. . |
| 4,784,149 | 11/1988 | Berman et al. . |
| 4,790,324 | 12/1988 | O'Hara et al. . |
| 4,797,840 | 1/1989 | Fraden . |
| 4,831,258 | 5/1989 | Paulk et al. . |
| 4,895,164 | 1/1990 | Wood . |
| 4,907,895 | 3/1990 | Everest ........................ 374/130 |
| 4,932,789 | 6/1990 | Egawa et al. . |
| 5,018,872 | 5/1991 | Suszynski et al. ........................ 374/133 |

FOREIGN PATENT DOCUMENTS

| | | |
|---|---|---|
| 0201790 | 11/1986 | European Pat. Off. . |
| 1914468 | 11/1970 | Germany . |
| 0092535 | 10/1983 | Sweden . |
| 1425765 | 3/1973 | United Kingdom . |

OTHER PUBLICATIONS

Houdas et al., *Human Body Temperature* (Plenum Press: N.Y.), 83.
Det Tronics advertisement, *InTech*, 10/87, p. 48.
Dexter Research Center product description for the Model 1M Thermopile Detector, Oct. 1980.

*Primary Examiner*—Kyle L. Howell
*Assistant Examiner*—J. P. Lacyk
*Attorney, Agent, or Firm*—Hamilton, Brook, Smith & Reynolds

[57] ABSTRACT

Tympanic temperature measurements are obtained from the output of a radiation sensor mounted in an extension from a housing. The housing has a temperature display and supports electronics for responding to sensed radiation. The sensor is mounted in an improved extension which is shaped to fit into smaller ear canals, such as a child's ear canal or a swollen adult ear canal. Within the extension, the sensor is positioned in a highly conductive environment and receives radiation from an external target through a tube. Electronics determine the target temperature based on the sensor output signal and a temperature sensor signal.

49 Claims, 11 Drawing Sheets

CALCULATE OUTPUT PROCEDURE

A/D CONVERSION INTERRUPT SERVICE ROUTINE

RADIATION DETECTOR PROBE

RELATED APPLICATIONS

This is a Continuation-in-part of application Ser. No. 07/646,855, filed Jan. 28, 1991 for "RADIATION DETECTOR HAVING IMPROVED ACCURACY" now U.S. Pat. No. 5,99,436 which is a divisional of application Ser. No. 07/338,968 filed Apr. 14, 1989, now U.S. Pat. No. 5,012,813 which is incorporated herein by reference and which is a Continuation-in-part of application Ser. No. 07/280,546 filed Dec. 6, 1988 for "RADIATION DETECTOR SUITABLE FOR TYMPANIC TEMPERATURE MEASUREMENT", now U.S. Pat. No. 4,993,419 which is incorporated herein by reference.

BACKGROUND

Radiation detectors which utilize thermopiles to detect the heat flux from target surfaces have been used in various applications. An indication of the temperature of a target surface may be provided as a function of the measured heat flux. One such application is the testing of electrical equipment. Another application has been in the scanning of cutaneous tissue to locate injured subcutaneous regions. An injury results in increased blood flow which in turn results in a higher surface temperature. Yet another application is that of tympanic temperature measurement. A tympanic device relies on a measurement of the temperature of the tympanic membrane area in the ear of an animal or human by detection of infrared radiation as an alternative to traditional sublinqual thermometers.

SUMMARY OF THE INVENTION

An improved tympanic temperature measurement device is presented in U.S. Pat. No. 4,993,419. That device provides for accuracy within one-tenth of a degree over limited ranges of ambient temperature with a relatively large probe and wide field of view, which for some users makes it difficult to measure tympanic temperature in adults, and in small children. An object of the present invention is to provide a tympanic temperature measurement device which would provide accuracy ear anatomies, including including infants and provide for greater ease of use to within one-tenth degree over a wide range. In obtaining that accuracy, the present invention continues to avoid any requirement for a reference target or for control of the temperature of the radiation sensor as such requirements had resulted in complexity and difficulties in prior tympanic temperature measurement devices.

A radiation detector comprises a radiation sensor such as a thermopile and a thermal mass enclosing the thermopile. The thermal mass includes an elongated thermally conductive tube of a first internal diameter. The tube extends from the distal end of the detector to a rear volume of larger internal diameter in which the sensor is mounted. In one device, the tube is gold plated and is thus highly reflective. In another device the tube is plated with a metal oxide for high absorption of radiation. A window is mounted adjacent to an end of the tube.

In accordance with one feature of the present invention, the portions of the thermal mass forming the tube and rear volume are formed in a unitary structure of high thermal conductivity material. The unitary thermal structure has an outer surface with an outer diameter at its distal end which is less than an outer diameter about the rear volume. The outer surface is tapered about the tube such that a unitary thermal mass of increasing outer diameter is provided about the end of the tube adjacent to the rear volume. The unitary thermal mass maximizes conductance and thermal mass within a limited diameter. To avoid changes in fixtures used in mounting the thermopile within the unitary thermal structure, in one embodiment the thermal structure is of limited diameter and may be supplemented with an additional thermal mass. The additional thermal mass surrounds the rear volume and a portion of the tube and is in close thermal contact with the unitary thermal structure. In another embodiment, the unitary thermal structure extends from the distal end of the detector to a housing such that no additional thermal mass is required.

It has been found that a narrow field of view radiation detector provides a more accurate and reliable reading of tympanic temperature. In the detector of the present invention, that field of view is obtained by controlling the reflectance of the inner surface of the tube, the length and diameter of the tube and the position of the thermopile behind the tube. In one embodiment, the tube has a reflective inner surface providing a field of view from the thermopile of about sixty degrees or less. A field of view of less than about sixty degrees allows for viewing of only a portion of the ear canal within less than about 1 centimeter of the tympanic membrane. In another embodiment, the tube has a nonreflective inner surface which produces a field of view from the thermopile of about thirty degrees or less. In either embodiment, the thermopile response may be fine tuned by changing the position of the thermopile behind the tube which changes the field of view and alters the thermopile response signal level.

In accordance with another aspect of the present invention, the infrared radiation sensor is mounted in the rear volume within the unitary thermal mass. The sensor has an active area influenced by radiation from an external target and a reference area of known temperature which is substantially unaffected by radiation. The sensor is preferably a thermopile having its cold junction reference area thermally coupled to the thermal mass but it may be a pyroelectric device. The thermally conductive tube is thermally coupled to the thermal mass and passes radiation to the sensor from the external target. A thermal barrier surrounds the thermal mass and tube. The temperature of the thermal mass, and thus of the sensor reference area, is allowed to float with ambient. A temperature measurement of the thermal mass is made to compensate the sensor output.

Temperature differences between the tube and sensor reference area would lead to inaccurate readings. To avoid those differences, the large unitary thermal mass minimizes temperature changes from heat which passes through the thermal barrier, and good conductivity within the mass increases conductance and minimizes temperature gradients. The outer thermal RC time constant for thermal conduction through the thermal barrier to the thermal mass and tube is at least two, and preferably at least three orders of magnitude greater than the inner thermal RC time constant for the temperature response of the reference area to heat transferred to the tube and thermal mass. For prompt readings, the inner RC time constant should be about $\frac{1}{2}$ second or less.

Preferably, the thermally conductive tube is thermally coupled to the sensor by a thermally conductive material such as epoxy. In accordance with the present invention, the amount of thermally conductive material is tuned to the detector to minimize the response of the sensor to undesired thermal perturbations of the tube. Providing an insufficient amount of material causes a positive error response from the sensor for thermal perturbations, while too much material causes a negative error response from the sensor for thermal perturbations. By providing the proper amount of material between the sensor and the tube, the added thermal conductance from the material tunes the reference area and the active area of the sensor to respond in phase to thermal perturbations such that the sensor response is substantially unaffected by said perturbations.

In the radiation detector of the present invention, the radiation sensor and the tube are positioned in an extension which is particularly suited for obtaining tympanic temperature measurements. To accomplish this, the extension is inserted into a subject's ear, and preferably into the ear canal. Once inserted, the extension is pivoted and the sensor scans the ear canal and senses the emitted radiation. The detector employs electronics which detects the peak radiation sensed by the sensor and converts it to a tympanic temperature indication.

The probe extension which supports the radiation sensor extends from a housing which displays the tympanic temperature. The housing extends along a first axis and the extension preferably extends at an angle of about 75 degrees from the first axis. This housing supports the battery powered electronics for converting radiation sensed by the sensor to tympanic temperature displayed by the display. The electronics included a processor for providing the displayed temperature based on radiation received from the tympanic membrane. If the sensor receives radiation from the cooler outer ear instead of the tympanic membrane, the processor determines the displayed temperature as a function of the received radiation compensated by an indication of ambient temperature to produce a core temperature approximation. The entire instrument is housed in a single hand-held package. The small additional weight of the electronics in the hand-held unit is acceptable because readings can be made quickly.

In accordance with another aspect of the present invention, the probe extension is adapted to be inserted into an ear canal. More specifically, the diameter of the distal tip as well as the shape and taper of the extension may be set to provide a detector useful in normal adult ear canals or a pediatric detector useful in small ear canals, especially children's ear canals, and swollen adult ear canals. To that end, the extension has a diameter of about 3–8 mm about its distal end and a substantially conical shape increasing in diameter along its length from its distal end and characterized by an included angle of about 25–60 degrees. As such, the extension is capable of being inserted into an ear canal up to one-third of the length of the ear canal.

In a pediatric detector embodiment the conical shape of the extension has an included angle of about forty degrees. Further, the diameter of the tip of the distal end of the extension is preferably in the range of 3–6 mm. As such, the pediatric detector is particularly useful on subjects having small ear canals but is also useful on adult subjects. In another embodiment the conical portion of the extension has an included angle of about thirty degrees. The diameter of the tip of the distal end of the extension is no more than about 7 mm. As such, the detector is particularly useful on adult subjects having normal ear canals, but it may also be used on children.

The radiation sensor assembly of a preferred embodiment includes a sensing device which is mounted within a rigid structure of high thermal conductivity such as beryllium oxide and has its reference area thermally coupled thereto. The passage through a thermally conductive tube passes thermal radiation from the external target, such as a tympanic membrane, to the thermopile. A window is mounted on the rigid structure such that it is in close thermal contact with the structure.

In one embodiment of the present invention, a detector comprises a substantially conical extension employing the above-described radiation sensor assembly. Preferably, the sensor assembly includes a thermopile sensor. In this embodiment, the tube provides a field of view from the thermopile of about thirty degrees or less. A thermal mass of high thermal conductivity material surrounds the tube and encloses the rigid structure in a rear volume. The thermal mass has a region within the rear volume which is defined between a rearwardly facing surface of the thermal mass and forward a face of the window. The region is preferably filled with air, providing a low thermal conductivity environment therein. The high thermal conductivity mass provides close thermal contact among the tube, the rigid structure, the thermopile cold junction and the ends of the window. As such, a continuous low thermal resistance path is formed from the tube to the cold junction of the thermopile and the window is held to the cold junction temperature.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DESCRIPTION OF A PREFERRED EMBODIMENTS

Figure 1:
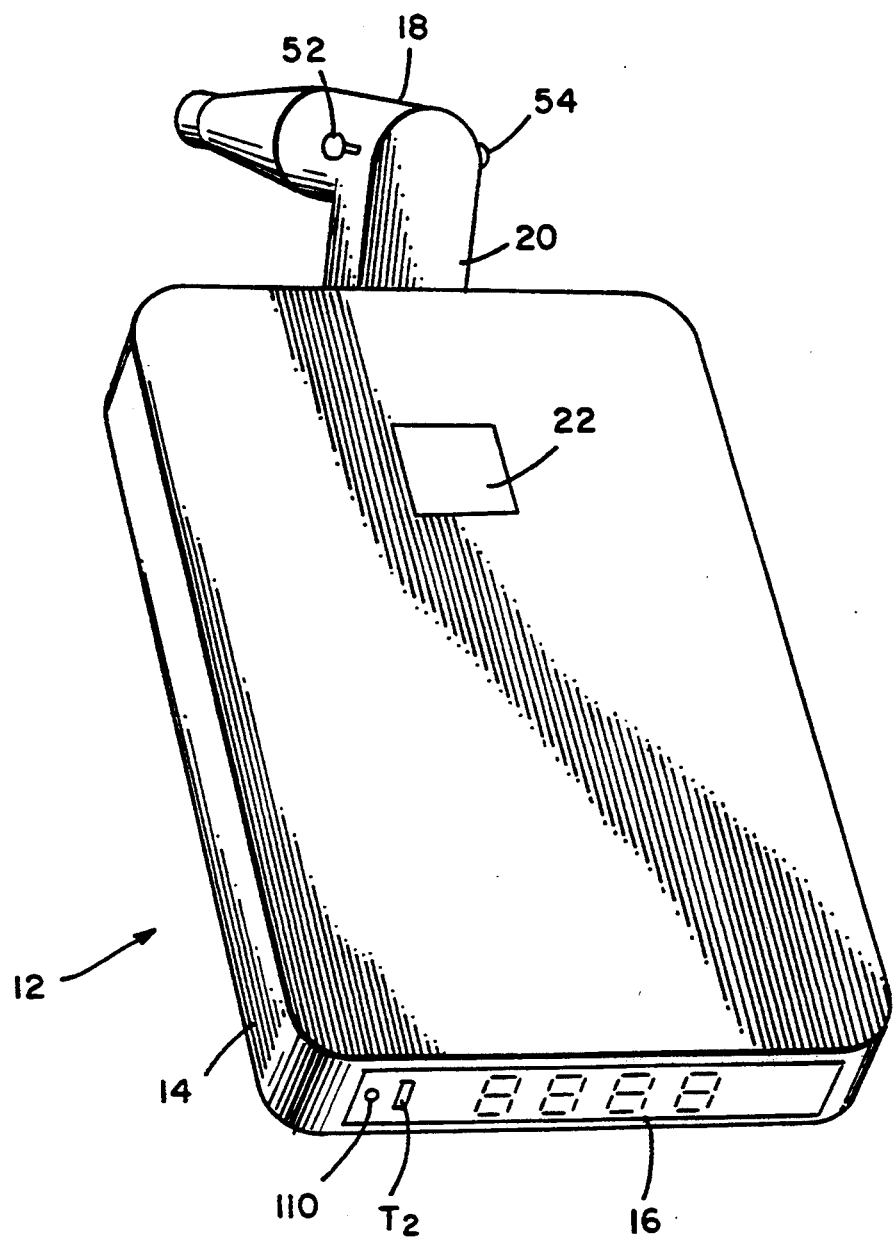
FIG. 1 illustrates one embodiment of a radiation detector for tympanic temperature measurements in accordance with the present invention.

In one embodiment of the present invention, the radiation detector 12 of FIG. 1 includes a flat housing 14 with a digital display 16 for displaying a tympanic temperature measurement. Although the display may be located anywhere on the housing, it is preferred that it be positioned on the end so the user is not inclined to watch it during a measurement. The instrument makes an accurate measurement when pivoted to scan the ear canal, and the user should concentrate on only the scanning motion. Then the display can be read. A thermopile radiation sensor is supported within a probe 18 at the opposite end of the housing 14. The housing extends along a first axis 19 (FIG. 2) and the extension 18 extends orthogonally from an intermediate extension 20 which extends at an angle of about 15 degrees from the first axis. As such, the extension 18 extends at an angle of about 75 degrees from the first axis 19 of the housing. Thus, the head of the detector, including the extension 18 and 20, has the appearance of a conventional otoscope. An on/off switch 22 is positioned on the housing.

Figure 2:
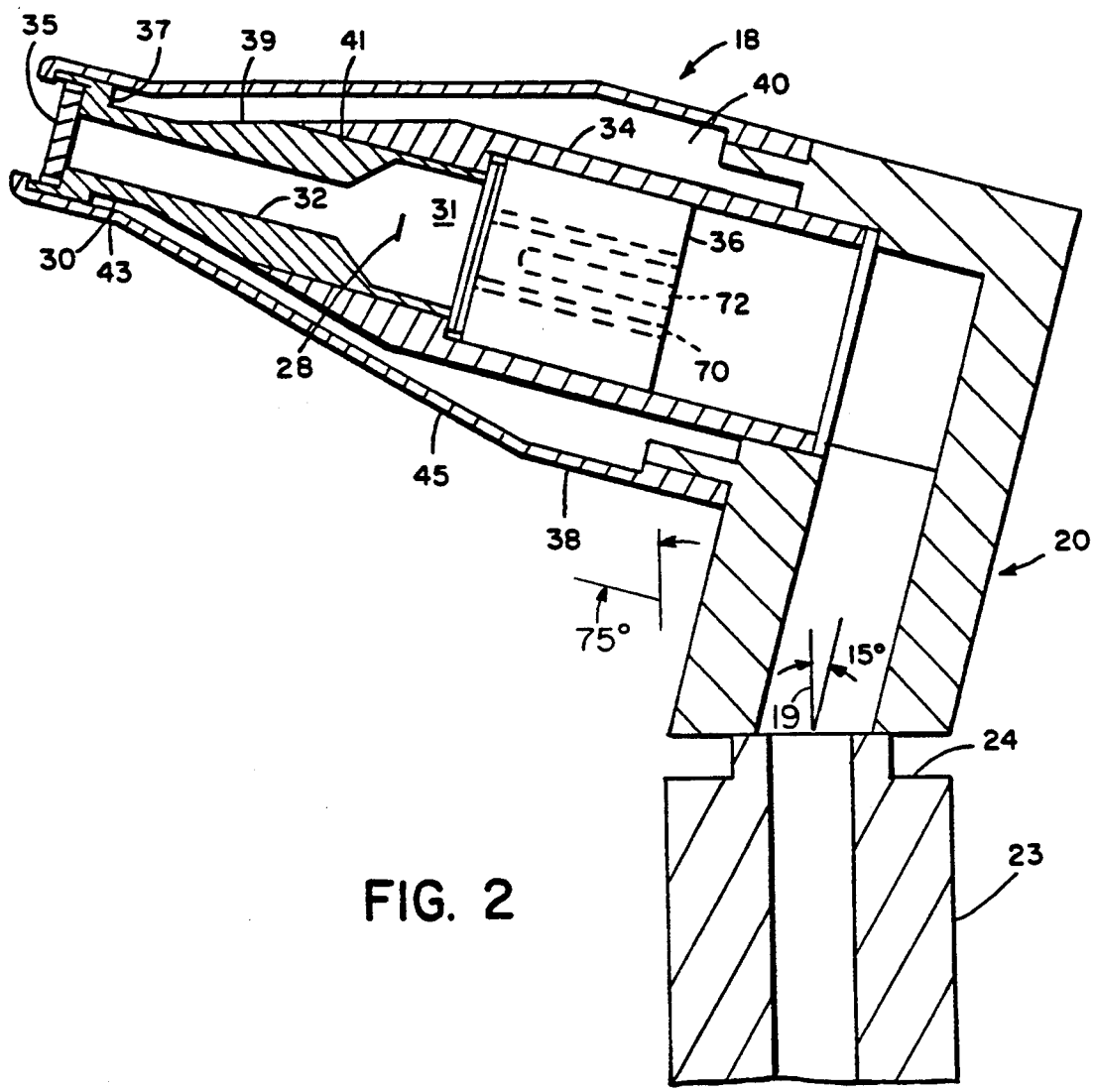
FIG. 2 is a cross-sectional view of the extension of the detector of FIG. 1 in which the thermopile radiation sensor is positioned.

A cross-sectional view of the extension of the detector of FIG. 1 is illustrated in FIG. 2. A base portion 23 is positioned within the housing 14, and the housing clamps about a groove 24. As noted, the portion 20 extends at about a 15 degree angle from the first axis 19 and thus from the base portion 23. Further, the extension 18 extends at about a 75 degree angle from the first axis. The extension 18 is tapered toward its distal end at 26 so that it may be comfortably positioned in the ear canal to view the tympanic membrane and/or ear canal.

A preferred disposable element to be used over the extension 18 is presented in the '419 patent and will not be discussed here.

The edge at the end of the probe is rounded so that when the probe is inserted into the ear it can be pivoted somewhat without discomfort to the patient. The probe is also curved like an otoscope to avoid interference with the ear. By thus pivoting the probe, the ear canal is scanned and, at some orientation of the probe during that scan, one can be assured that the maximum temperature is viewed. Since the ear canal cavity leading to the tympanic area is the area of highest temperature, the instrument is set in a peak detection mode, and the peak detected during the scan is taken as the tympanic temperature.

An improved assembly within the extension 18 is illustrated in FIG. 2. A thermopile 28 is positioned within a can 30 of high conductivity material such as copper. The conductivity should be greater than two watts per centimeter per degree Kelvin. The can is filled with a gas of low thermal conductivity such as Xenon. The thermopile 28 is positioned within a rear volume 31. It is mounted to an assembly which includes a flange 33. The volume is sealed by cold welding of the flange 33 to a flange 41 extending from the can. Cold welding is the preferred approach to making the seal and, to utilize past welding fixtures, the outer diameter of the can is limited.

The thermopile views the tympanic membrane area through a radiation guide 32. The radiation guide 32 is gold plated to minimize oxidation. It is closed at its forward end by a germanium window 35. To minimize expense, the window is square with each side slightly longer than the diameter of the radiation guide 32. The window is cemented with epoxy within a counterbore in a flange 37 at the end of the radiation guide. The epoxy serves as a gas seal and mechanical support for the somewhat brittle germanium window. The flange serves to protect the germanium window should the detector be dropped. The diagonal of the window is less than the diameter of the counterbore, and its thickness is less than the depth of the counterbore. Therefore, if the detector is dropped, any force which presses the plastic housing toward the window is absorbed by the flange. The germanium need only withstand the forces due to its own inertia.

Whereas the detector disclosed in the '419 patent had a field of view of about 120°, it has been determined that a narrower field of view of about sixty degrees or less provides the user with an easire and more accurate indication of tympanic temperature. With a narrower field of view, the thermopile flake, when directly viewing the tympanic membrane, also views less than about one centimeter along the ear canal wherein the tissue is at substantially the same temperature as the tympanic membrane. A better view of the tympanic membrane also results from the cylindrical extension 43 beyond the conical portion of the extension 18. With the ear canal straightened by the probe, the extension 43 can extend well into the ear canal beyond any hair at the canal opening.

The tympanic membrane is about 2.5 centimeters from the opening of the ear canal. The ear canal for an adult subject is typically about 8 mm wide, so the diameter of the tip of the extension is no more than about 8 mm wide. The conical portion of the extension 18 prevents the tip of the extension from extending more than about eight millimeters into the ear canal. Beyond that depth, the patient suffers noticeable discomfort. With a field of view of less than about sixty degrees, the ear canal is viewed more than about about eight millimeters from the tip of the extension 18. Thus, only the ear canal within less than 9 millimeters of the tympanic membrane is viewed as the radiation guide is directed toward the membrane. The result is a more accurate and reliable reading of the tympanic temperature which is essentially core temperature.

With the present instrument, the narrow field of view is obtained by two changes to the prior radiation guide. The reflectivity within the guide is reduced. Radiation entering the tube at greater angles must be reflected a greater number of times from the radiation guide before reaching the thermopile flake. With the higher emissivity, such radiation is less likely to reach the flake to be detected. The field of view is further decreased by extending the enlarged rear volume between the flake and the radiation guide. Radiation which enters the radiation guide at greater angles, yet travels through the radiation guide, leaves the guide at greater angles and is thus unlikely to be viewed by the flake. The length of the radiation guide is another parameter which affects the field of view. By using a planoconvex lens as the window 35, the field of view can be further limited.

Both of the above approaches to decreasing the field of view increase the amount of heat which is absorbed by the can in which the thermopile is mounted. The added heat load adds to the importance that the can, including the radiation guide, have a large thermal mass and high thermal conductivity as discussed below.

As distinguished from the structure presented in the '419 patent, the volume 31 surrounding the thermopile and the radiation guide are formed of a single piece of high conductivity copper. This unitary construction eliminates any thermal barriers between the foremost end of the radiation guide and the portion of the can surrounding the thermopile which serves as the cold junction of the thermopile. Further, at least a portion of added thermal mass which surrounds the radiation guide is unitary with the can as well. Specifically, a taper 39 results in an enlarged region 41 which serves as a thermal mass in accordance with the principals of the parent application. The taper 39 continues along a conductive thermal mass 34 which surrounds the can and a conductive plug 36. Both the mass 34 and plug 36 are of copper and are in close thermal contact with the can 30.

The outer sleeve 38 of the extension 18 and the intermediate extension 20 are of plastic material of low thermal conductivity. The sleeve 38 is separated from the can 30 and thermal mass 34 by an insulating air space 40. The taper of the can 30 and thermal mass 34 permits the insulating space to the end of the extension while minimizing the thermal resistance from the end of the tube 32 to the thermopile, a parameter discussed in detail below. The inner surface of the plastic sleeve 38 may be coated with a good thermal conductor to distribute across the entire sleeve any heat received from contact with the ear. Twenty mils of copper coating would be suitable.

In contrast with the prior design, the portion of the sleeve 38 at the foremost end of extension 18 has a region 43 of constant outer diameter before a tapered region 45. The region of constant outer diameter reduces the outer diameter at the distal end and minimizes interference when pivoting the extension in the ear to view the tympanic membrane area. The tapered region is spaced six millimeters from the end of the extension to allow penetration of the extension into the ear canal by no more than about eight millimeters.

One of the design goals of the device was that it always be in proper calibration without requiring a warm-up time. This precluded the use a heated target in a chopper unit or heating of the cold junction of the thermopile as was suggested in the O'Hara et al. U.S. Pat. No. 4,602,642. To accomplish this design goal, it is necessary that the system be able to operate with the thermopile at any of a wide range of ambient temperatures and that the thermopile output have very low sensitivity to any thermal perturbations.

The output of the thermopile is a function of the difference in temperature between its warm junction, heated by radiation, and its cold junction which is in close thermal contact with the can 30. In order that the hot junction respond only to radiation viewed through the window 35, it is important that the radiation guide 32 be, throughout a measurement, at the same temperature as the cold junction. To that end, changes in temperature in the guide 32 must be held to a minimum, and any such changes should be distributed rapidly to the cold junction to avoid any thermal gradients. To minimize temperature changes, the tube 32 and the can 30 are, of course, well insulated by means of the volume of air 40. Further, a high conductance thermal path is provided to the cold junction. This conductance is enhanced by the unitary construction. Further, the can 30 is in close thermal communication with the thermal masses 34 and 36, and the high conductivity and thickness of the thermal masses increase the thermal conductance. A high thermal conductivity epoxy, solder or the like joins the can and thermal masses. The solder or epoxy provides a significant reduction in thermal resistance. Where solder is used, to avoid damage to the thermopile which is rated to temperatures of 125° C., a low temperature solder of indium-tin alloy which flows at 100° C. is allowed to flow into the annular mass 34 to provide good thermal coupling between all elements.

The thermal resistance from the outer surface of the plastic sleeve 38 to the conductive thermal mass is high to minimize thermal perturbations to the inner thermal mass. To minimize changes in temperature of the guide 32 with any heat transfer to the can which does occur, the thermal mass of the can 30, annular mass 34 and plug 36 should be large. To minimize thermal gradients where there is some temperature change in the tube during measurement, the thermal resistance between any two points of the thermal mass should be low.

Thus, due to the large time constant of the thermal barrier, any external thermal disturbances, such as when the extension contacts skin, only reach the conductive thermal mass at extremely low levels during a measurement period of a few seconds; due to the large thermal mass of the material in contact with the cold junction, any such heat transfer only causes small changes in temperature; and due to the good thermal conductance throughout the thermal mass, any changes in temperature are distributed quickly and are reflected in the cold junction temperature quickly so that they do not affect temperature readings.

The thermal RC time constant for thermal conduction through the thermal barrier to the thermal mass and tube should be at least two orders of magnitude greater than the thermal RC time constant for the temperature response of the cold junction to heat transferred to the tube and thermal mass. The RC time constant for conduction through the thermal barrier is made large by the large thermal resistance through the thermal barrier and by the large thermal capacitance of the thermal mass. The RC time constant for response of the cold junction is made low by the low resistance path to the cold junction through the highly conductive copper can and thermal mass, and the low thermal capacitance of the stack of beryllium oxide rings and pin conductors to the thermopile.

Although the cold junction capacitance is naturally low, there are size constraints in optimizing the thermal capacitance of the thermal mass, the thermal resistance through the thermal barrier and the internal thermal resistance. Specifically, the external thermal resistance can be increased by increased radial dimensions, the capacitance of the thermal mass can be increased by increasing its size, and the thermal resistance through the longitudinal thermal path through the tube can be decreased by increasing its size. On the other hand, the size must be limited to permit the extension to be readily positioned and manipulated within the ear.

Besides the transfer of heat from the environment, another significant heat flow path to the conductive thermal mass is through leads to the system. To minimize heat transfer through that path, the leads are kept to small diameters. Further, they are embedded in the plug 36 through bores 70; thus, any heat brought into the system through those leads is quickly distributed throughout the thermal mass, and only small changes in temperature and small gradients result.

Because the temperature of the thermal mass is not controlled, and the response of the thermopile 28 is a function of its cold junction temperature, the cold junction temperature must be monitored. To that end, a thermistor is positioned at the end of a central bore 72 in the plug 36.

Figure 3:
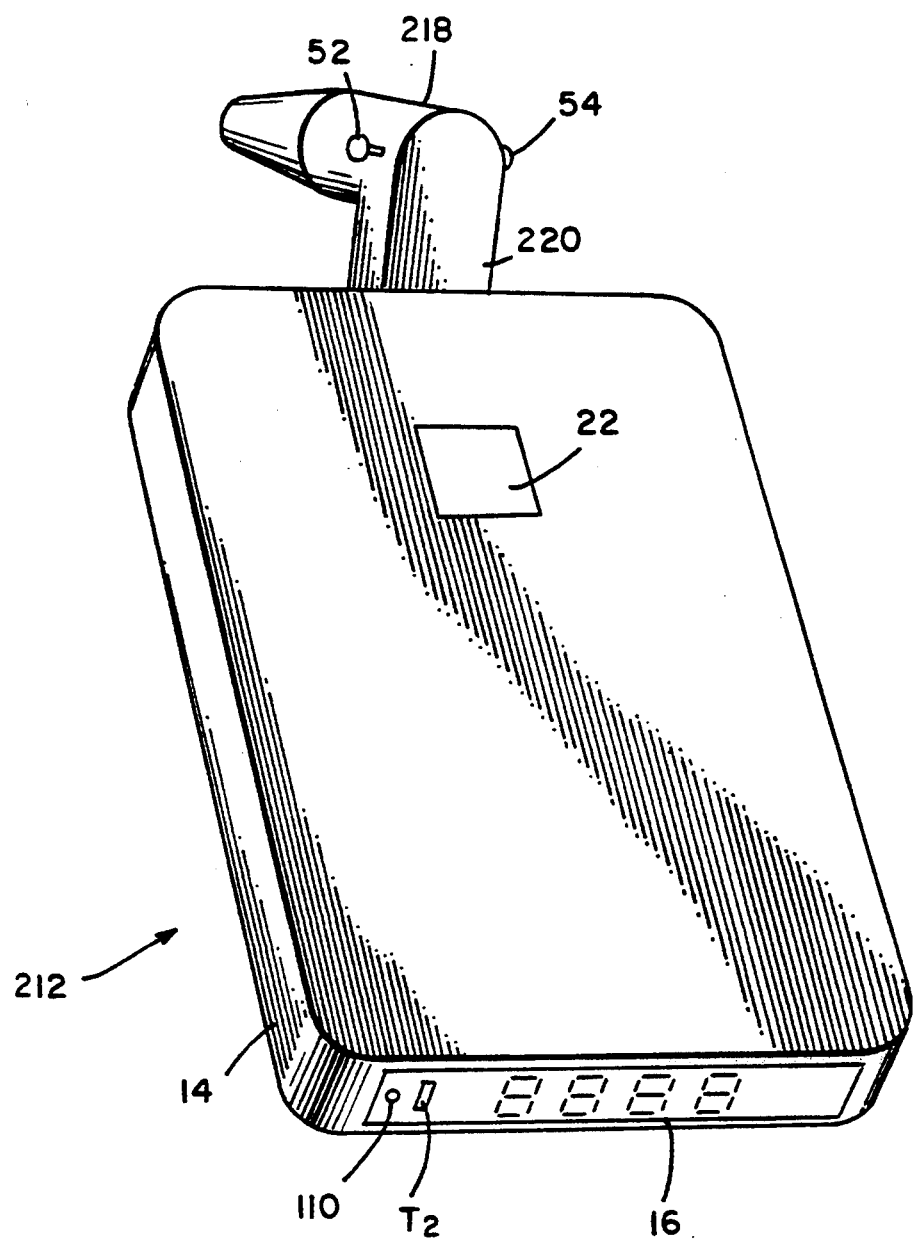
FIG. 3 illustrates another embodiment of the radiation detector for tympanic temperature measurements in accordance with the present invention.
Figure 4:
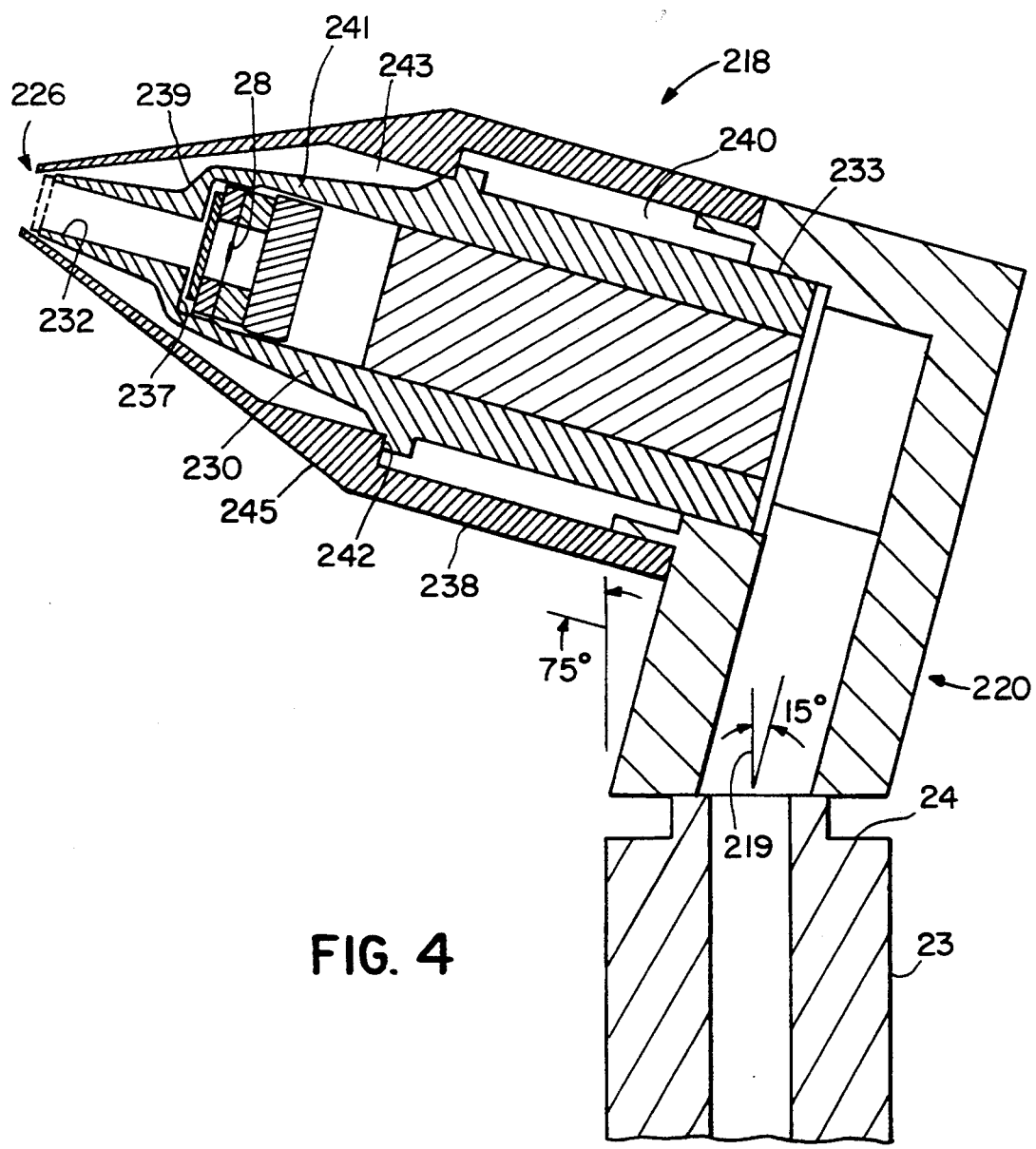
FIG. 4 is a cross-sectional view of the extension of the detector of FIG. 3 in which the thermopile radiation sensor is positioned.

Another embodiment of the present invention is illustrated in FIG. 3. The radiation detector 212 employs a thermopile radiation sensor supported within a probe extension 218 of the opposite end of the housing 14. As shown in FIG. 4, the extension 218 extends at an angle of about 75 degrees from a first axis 219 along which the housing extends. The extension 218 is tapered along its length from its distal end, making the instrument 212 particularly useful in obtaining tympanic temperature measurements without causing the subject discomfort.

As previously discussed, the other embodiment provided an extension with a constant diameter tip which works well in ear canals of about the same diameter. However, this tip does not fit within smaller ear canals, and subjects with larger diameter ear canals will suffer discomfort as the constant diameter tip of the extension contacts the walls of their ear canals during pivoting to scan the ear canal. In accordance with the present invention, the substantially conical shaped extension 218 has an increasing diameter along a portion of its length from its distal end such that the extension may be inserted into an ear canal without causing discomfort. Once inserted, the extension 218 is pivoted to scan the ear canal adjacent to and including the tympanic membrane. The conical shape of the extension 218 ensures that the edge of the tip of the extension is unable to contact the walls of the ear canal. The thermopile 28 senses radiation within the ear canal during the pivotal rotation of the extension 218. The detector 212 employs electronics in the housing 14 for detecting the peak radiation sensed by the sensor 28 and converting it to a tympanic temperature indication. Further, the electronics may also provide an audible tone indicating that peak radiation has been detected for a particular measurement period. The variable tone or variable pulse signal allows a user to know when to stop pivoting the extension for a given subject.

Figure 5:
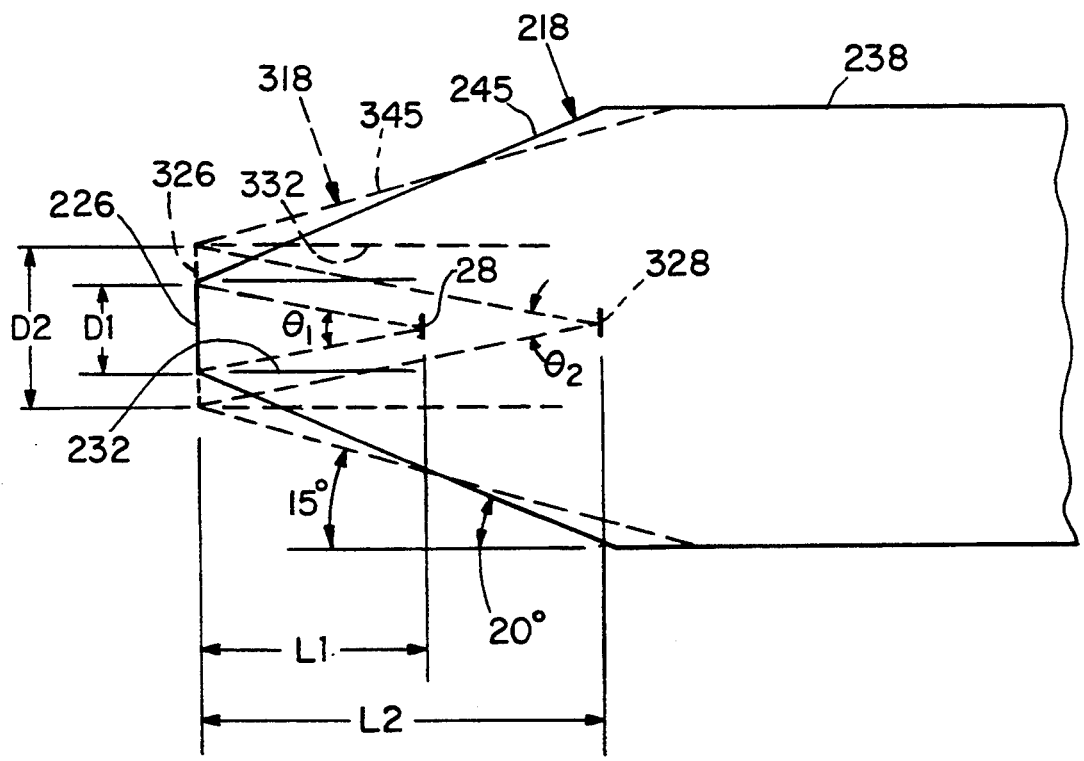
FIG. 5 is a profile of pair of configurations of the extension of FIG. 4.

The diameter of the distal tip of the probe extension as well as its taper may be selected to provide a detector useful in normal ear canals or a pediatric detector useful in small ear canals. In one configuration, as shown in FIG. 5, the extension 218 has a small diameter tip and is tapered along its length at its distal end making the extension particularly suited for insertion into small ear canals. A small ear canal is about 3-6 mm wide, so the diameter of the extension 218 along the portion of its length from its distal tip 226 is no more than about 3-6 mm. Further, the extension 218 comprises an outer sleeve 238 with a tapered portion 245 extending at a twenty degree angle from the distal tip 226. As such, the conical portion 245 of the extension has an included angle of about forty degrees. With a preferred 3.4 mm outer diameter at the tip 226 and a forty degree included angle along the conical portion 245, the extension 218 is capable of being inserted about 4 mm into a small ear canal. A young child's ear canal is about 10 mm in length, so the extension may be inserted into the child's ear canal up to about one-third of the length of the ear canal without causing discomfort.

In another configuration, indicated by dashed lines in FIG. 5, an extension 318 has a larger diameter tip and is tapered such that the extension is particularly suited for normal ear canals including adult ear canals and ear canals of older children. A normal ear canal is about 8 mm wide, and the diameter of the extension 318 about its distal tip 326 is no more than 7 mm. The tapered portion 345 of the outer sleeve extends at about a fifteen degree angle from the distal tip 326 which corresponds to a thirty degree included angle. As such, the extension 318 having a preferred tip diameter of about 5 mm is capable of being inserted about 8 mm into a normal ear canal, or about one-third of the length into the canal without causing the subject discomfort.

Referring to FIG. 5, the extensions 218 and 318 have different profiles which were selected to minimize discomfort to the subject and to provide for accurate tympanic temperature readings. To that end, the diameter of the tip of the extensions is specified and depends on the diameter of the subject's ear canal. Further, the extensions are configured to provide a field of view of about thirty degrees which provides more accurate readings as explained below. Thus, to provide a thirty degree field of view at $\theta_1$, with a 3 mm inner diameter of tube 232, the length 21 from the tip 226 to the thermopile 28 is about 7.5 mm. Due to the proximity of the thermopile 28 to the tip (7.5 mm), the extension 218 requires the steeper taper of 20 degrees so that the thermopile assembly (not shown) fits into the extension. Also, the taper of 20 degrees provides a necessary stop in close proximity to the distal end 226 for preventing insertion of the extension 218 too far into a short ear canal so as to cause discomfort. To achieve the thirty degree field of view at $\theta_2$ with a tube 322 diameter of about 4.5 mm, a length of L2 of about 11 mm is required. Due to the larger diameter tip 326, the thermopile 328 is further from the tip for the same field of view so that the conical portion 345 may have a 15 degree taper. An adult canal has a flap of cartilage at the outer region of the ear (the concha). Thus, the conical portion 345 having the 15 degree taper is advantageous as it allows the extension 318 to be narrower and thus be inserted past the cartilage and extend into the ear canal.

An improved assembly within the extension 218 is shown in FIG. 4. A thermopile 28 is positioned within a thermal mass 230 formed of high thermal conductivity material such as copper. In contrast to the previous embodiment, the thermal mass 230 is a one-piece structure which mounts into a bore 233 within a portion 220 of the extension 218. Further, no contact between the thermal mass 230 and the outer sleeve 238 is made at the distal end 226 of the extension. Instead, a ridge 242 in the mass 230 contacts the sleeve 238 to achieve alignment of the mass and the distal end of the sleeve. The thermopile 28 is located in a rear volume 231 and views the tympanic membrane area through a conductive tube 232 formed in the mass 230.

Figure 7:
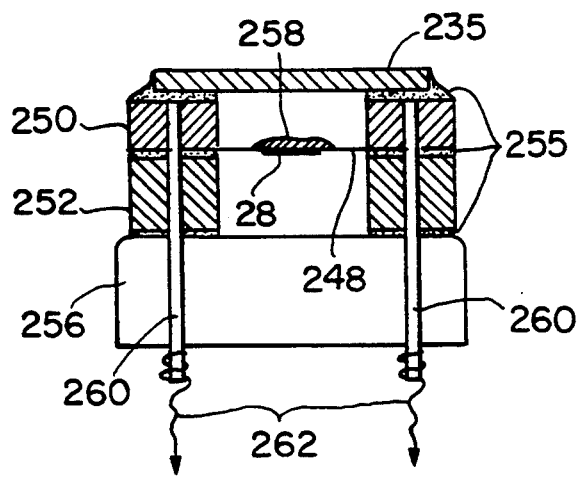
FIG. 7 is a cross-sectional view of a radiation sensor assembly of the detector of FIG. 6
Figure 6:
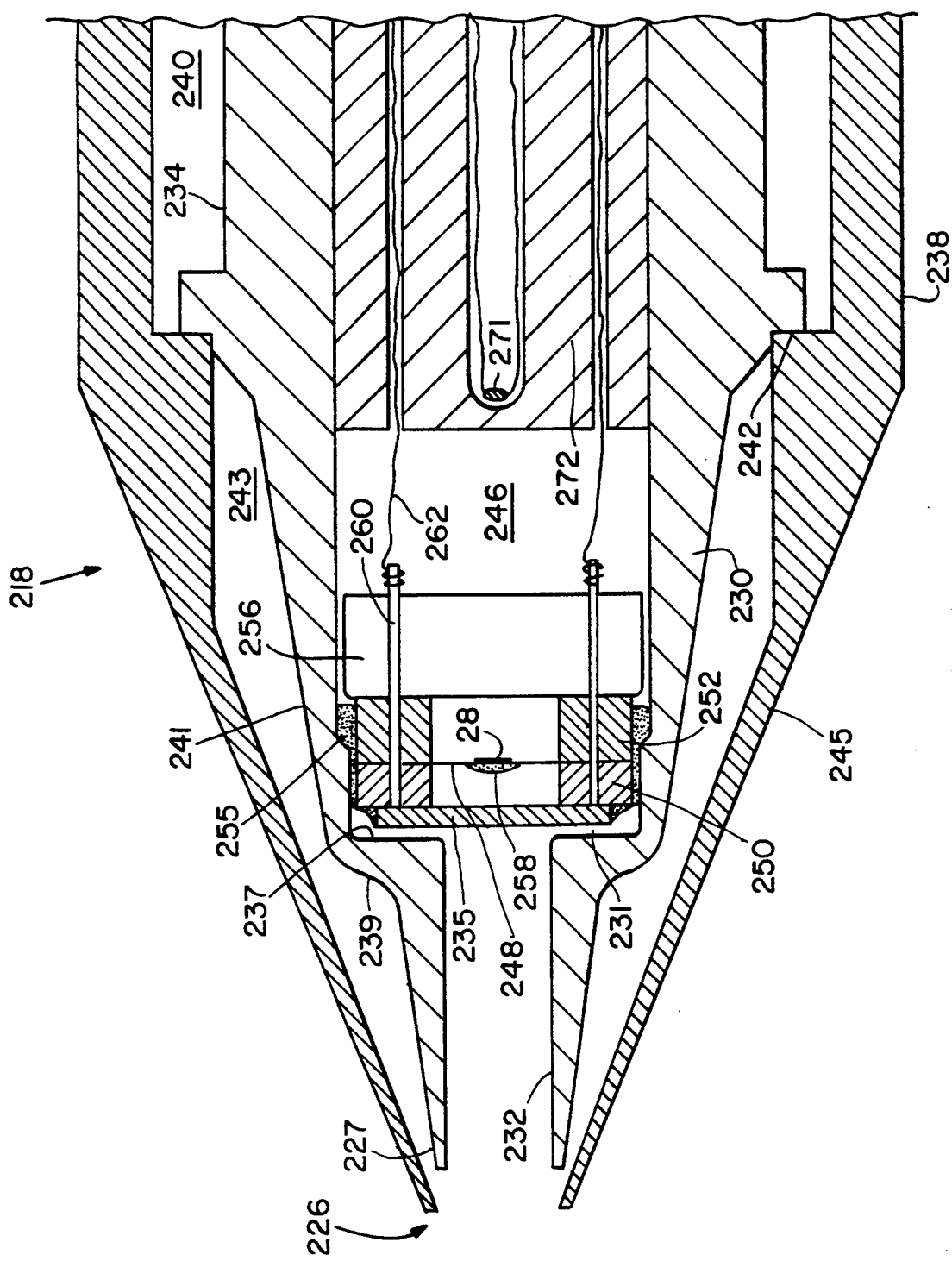
FIG. 6 is an enlarged cross-sectional view of the extension of FIG. 4.

Referring to FIGS. 6 and 7, the thermopile is mounted on the rear surface of a sheet of polytetrafluoroethylene 248 suspended from the rear surface of a first beryllium oxide ring 250. A mass of infrared absorbing black material 258 is positioned on the opposite surface of the sheet and serves as a radiation collector. A second beryllium oxide ring 252 supports the first ring 250 and the two rings are supported by a copper header 256. A window 235 formed of silicon or germanium is mounted on the first ring 250. The rings 250 and 252, the window 235 and the header 256 are thermally coupled by high thermal conductivity epoxy 255. A pair of leads 260 formed of 20 mils of kovar provide structural support to the assembly and provide a thermopile output signal to the electronics via a pair of 40 gauge wires 262. As such, the tube and the region defined by the surface 237 and the window 235 are filled with air. A sufficient amount of silver paint may be included within the rings to oxidize all air, and thus create a nitrogen environment in the gas tight region. Alternatively, but not preferably the window may be positioned at the distal end 226 of the housing 218 as indicated by the dashed lines. Having the window positioned directly on the sensor assembly minimizes temperature gradients between the window and thermopile.

It has been determined that a significantly narrower field of view provides the user with an easier and more accurate tympanic temperature indications. The detector disclosed in the '419 patent had a wide field of view of about 120° and the detectors disclosed in the '813 patent and described in the other embodiment have a field of view of about 60° or less. Thus, one object of this embodiment was to reduce the field of view to obtain a narrower field of view of about thirty degrees or less. To that end, the narrower field of view is obtained by plating the inner surface of the tube 232 with a layer of non-reflective material. Preferably, the non-reflective layer is a metal oxide such as nickel oxide or aluminum oxide. A metal oxide layer is employed because metal oxides are durable and will not change in properties if the inner surface of the tube is cleaned. Further, the metal oxide layer should be thin (a few tenths of thousanths of an inch) such that virtually no temperature gradient exists across the layer. The metal oxide surface absorbs substantially all radiation which strikes the tube 232 and allows radiation passing directly through the tube to reach the thermopile 28.

The dimensions of the tube 232 are chosen such that radiation entering the tube at angles of only up to fifteen degrees from the longitudinal axis of the tube passes directly to the thermopile. With the thirty degree field of view, the probe can easily be positioned such that substantially only the tympanic membrane may be viewed.

The above approach to decreasing the radiation gathering aperature size to about 3 mm and reducing the field of view to about thirty degrees significantly increases the noise level at the thermopile relative to the signal level. Further, this approach increases the amount of radiation which is absorbed by the thermal mass in which the thermopile is mounted. These two effects add to the importance that the thermal mass, including the tube, provide a large thermal mass and high thermal conductivity.

The thermal mass 230 is of unitary construction which eliminates thermal barriers between the tube 232 and the portion 241 of the thermal mass surrounding the thermopile 28. Further, a plug 272 of high thermal conductivity material positioned behind the thermopile 28 is in close thermal contact with the mass 230. The outer sleeve 238 is formed of low thermal conductivity plastic and is separated from the mass 230 by an insulating air space 240. The taper 239 of the mass 230 increases the insulating air space adjacent to the end of the extension 226 while minimizing thermal resistance from the tube 232 to the thermopile. The inner surface of the plastic sleeve 238 may be coated with a good thermal conductor to distribute across the entire sleeve any heat received from contact with the ear.

In order that the hot junction respond only to radiation viewed through the window 235, it is important that the tube 232 and the window 235 be, throughout a measurement, at the same temperature as the cold junction. The thermopile 28 acts as a thermal amplifier having a gain based on the number of junctions and the Seebeck coefficient. Thus, temperature gradients sensed by the thermopile are amplified by a factor of about 100. To minimize errors, changes in temperature in the tube 232 must be held to a minimum, and any such changes should be distributed rapidly to the cold junction to avoid any thermal gradients. To minimize temperature changes, the tube 232 and the mass 230 are well insulated by means of the volume of air 240. To avoid thermal gradients, the tube 232 is plated with a thin layer of high conductance non-reflectance metal oxide which minimizes temperature gradients across the layer. Further, the thermal mass 230 is thermally coupled to the rings 250 and 252 with high conductivity thermal epoxy 255 such that a high conductance thermal path is provided from the tube 232 to the cold junction. This conductance is enhanced by the unitary construction of the mass 230.

In accordance with another aspect of the invention, the amount of thermal epoxy 255 between the rings 250 and 252 and the mass 230 is tuned to the assembly to minimize the response of the thermopile 28 to undesired thermal perturbations at the end of the mass. Referring to FIG. 6, thermal variations in the air region 243 lead to heating of the tip 227 of the mass 230 which causes the inner surface of the tube 232 to emit radiation. If these thermal variations are not sensed by the cold junction via the high conductance thermal path from the tube 232 in phase with the sensing of the radiation by the hot junction, the thermopile 28 produces an error response.

Accordingly, the epoxy 255 may be incrementally added to adjust the high conductivity thermal path to the cold junction to bring the hot and cold junction thermal responses in phase. An insufficient amount of epoxy 255 causes a positive error response as the hot junction responds to thermal variations faster than the cold junction. Alternatively, too much epoxy 255 causes a negative error response as the cold junction responds faster to thermal variations than the hot junction. When the proper amount of epoxy has been provided, the tuned assembly produces no more than 0.1° thermopile response for up to 20° thermal variations during a test.

It has been determined in previous devices that a significant source of thermal gradients is caused by radiation from the window. To minimize these thermal gradients, the window 235 is mounted on the ring 250 with high thermal conductivity epoxy 255 such that it is thermally coupled to the cold junction. The epoxy provides a significant reduction in thermal resistance and provides good thermal coupling between all elements. On the other hand, conductance to the viewing region of the window should not be less than that to the cold junction. Thus, the window 235 is spaced from a rear face 237 of the mass 230 and its ends are spaced from the inner volume 231 by a low thermal conductivity air region. The region ensures that temperature gradients are distributed to the cold junction via the thermal mass and not directly through the window causing thermal gradients.

The thermal resistance from the outer surface of the plastic sleeve 238 to the conductive thermal mass 230 is high to minimize thermal perturbations to the inner thermal mass. The thermal mass is large to minimize changes in temperature of the tube 232 with any heat transfer to the mass which does occur. Further, the thermal resistance between any two points of the thermal mass 230, the tube 232, the window 235 or the rings 250 and 252 is low to minimize thermal gradients where there is some temperature change in the tube during measurement.

Thus, due to the large time constant of the thermal barrier 238, any external thermal disturbances, such as when the extension contacts skin, only reach the conductive thermal mass 230 at extremely low levels during a measurement period of a few seconds. Due to the large thermal mass of the materials in contact with the cold junction, any such heat transfer only causes small changes in temperature. Also, due to the good thermal conductance throughout the thermal mass, tube, window and rings any changes in temperature are distributed quickly and are reflected in the cold junction temperature quickly so that they do not affect temperature readings.

The thermal RC time constant for thermal conduction through the thermal barrier 238 to the thermal mass 230 and tube 232 is at least two orders of magnitude greater than the thermal RC time constant for the temperature response of the cold junction to heat transferred to the tube and thermal mass. The RC time constant for conduction through the thermal barrier 238 is made large by the large thermal resistance through the thermal barrier and by the large thermal capacitance of the thermal mass. The RC time constant for response of the cold junction is made low by the low resistance path to the cold junction through the highly conductive thermal mass, and the low thermal capacitance of the stack of beryllium oxide rings to the thermopile.

Besides the transfer of heat from the environment, another significant heat flow path in the system is through the leads 260. To minimize heat transfer through that path, the lead diameters are kept small and the leads 260 are trimmed off in the region 246. A pair of 40 gauge wires 262 are soldered to the shortened leads 260. The wires 262 extend from the region 246 through the plug 272 and provide thermopile signals to the electronics.

Yet another potential heat flow path in the system is through the header 256 to the plug 272. Since the header is in close thermal contact with the thermopile cold junction, any thermal gradients through the header 256 would be amplified 100 to 1000 times by the thermopile producing large error signals. In the present invention, the insulating region 246 of air is provided behind the header 256 to minimize heat transfer through that path. Thus, any thermal gradients in the plug would be forced to travel through the mass 230 and would be substantially dissipated without affecting the thermopile.

Because the temperature of the thermal mass 230 is not controlled and the response of the thermopile 28 is a function of its cold junction temperature, the cold junction temperature must be monitored. To that end, a thermistor 271 is positioned adjacent to the region 246 in the plug 272. The plug 272 is in thermal contact with the mass 230 such that the thermistor 271 is thermally coupled to the cold junction of the thermopile 28. However, the thermal path between the thermopile 28 and the thermistor has some thermal resistance. This resistance produces a temperature difference between the cold junction temperature and the sensed temperature which is not amplified. Therefore such error is not as significant as gradient errors amplified by the thermopile.

Figure 8:
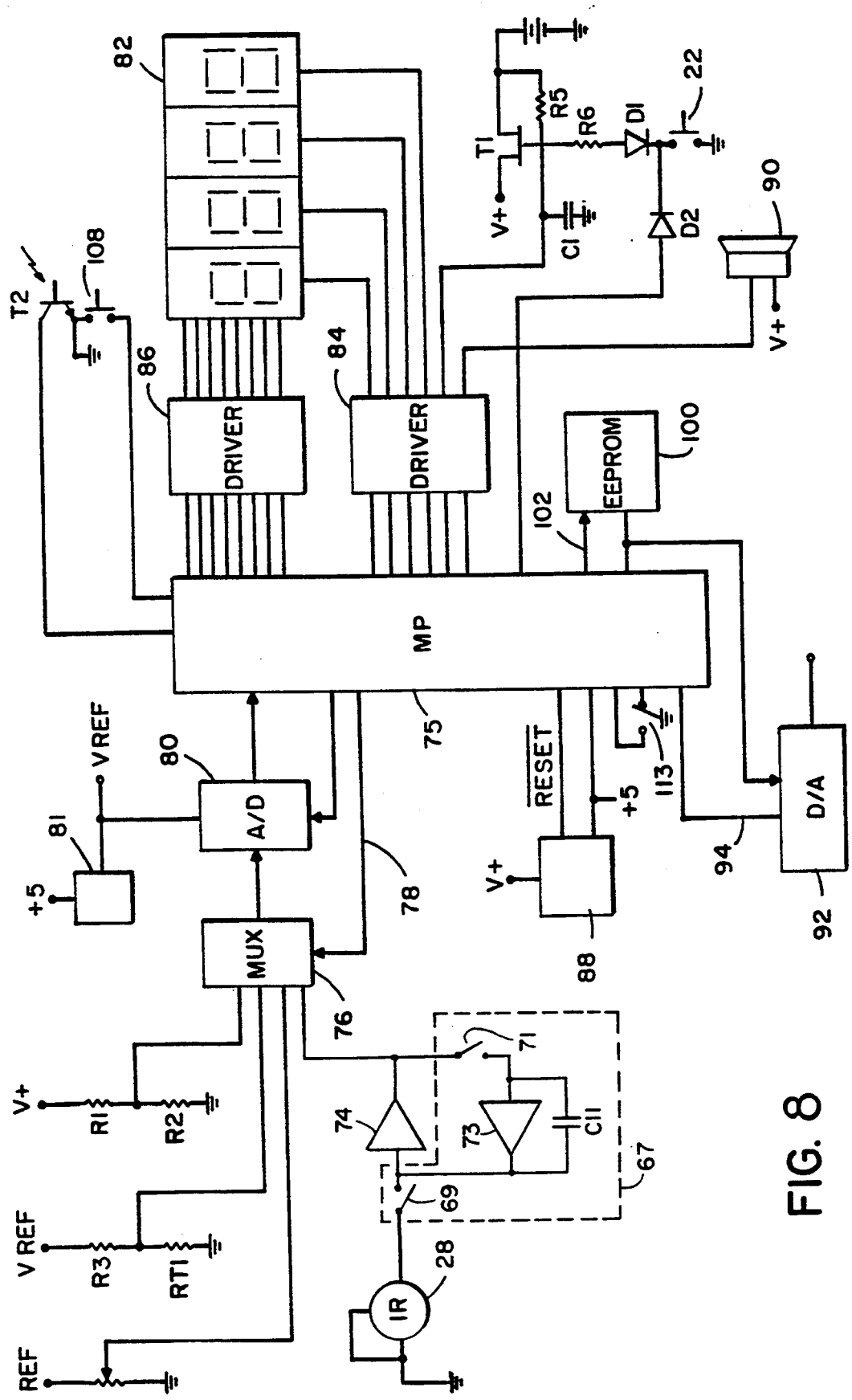
FIG. 8 is a block diagram of the electronic circuit of the detector of the present invention.

A schematic illustration of the electronics in the housing 14 of both embodiments of the present invention (FIGS. 1 and 3), for providing a temperature readout on display 16 in response to the signal from the thermopile, is presented in FIG. 8. The system is based on a microprocessor 73 which processes software routines included in read only memory within the processor chip. The processor may be a 6805 processor sold by Motorola.

The voltage generated across the thermopile 28 due to a temperature differential between the hot and cold junctions is amplified in an operational amplifier 74. For the detector of FIG. 1, the chopper circuit 67 is not employed and analog output from the amplifier 74 is applied as one input to a multiplexer 76. For the detector of FIG. 3, the thermopile output voltage is smaller so the amplifier 74 is configured in the chopper stabilized amplifier circuit 67. The circuit employs a switched feedback loop that removes internal offset voltages associated with the amplifier 74. The feedback loop comprises switches 69 and 71, an amplifier 73 and a storage capacitor C11. When the radiation detector is powered on, switch 69 is opened and switch 71 is closed. With this configuration, the feedback loop stores the offset voltage for the amplifier 74 in capacitor C11. The switch positions are then reversed such that the input signal to amplifier 74 is combined with the offset stored in the capacitor C11. The combined output is applied an an input to the multiplexer 76.

Another input to the multiplexer 76 is a voltage taken from a voltage divider R1, R2 which is indicative of the potential V+ from the power supply 78. A third input to the multiplexer 76 is the potential across a thermistor RT1 mounted in the bore 72 of block 36. The thermistor RT1 is coupled in a voltage divider circuit with R3 across a reference potential VRef. The final input to the multiplexer is a potential taken from a potentiometer R4 which may be adjusted by a user. The system may be programmed to respond to that input in any of a number of ways. In particular, the potentiometer may be used as a gain control or as a DC offset control.

At any time during the software routine of the microprocessor 73, one of the four inputs may be selected by the select lines 78. The selected analog signal is applied to a multiple slope analog system 80 used by the microprocessor in an integrating analog-to-digital conversion 80. The subsystem 80 may be a TSC500A sold by Teledyne. It utilizes the reference voltage VRef from a reference source 82. The microprocessor 73 responds to the output from the convertor 80 to generate a count indicative of the analog input to the convertor.

The microprocessor drives four 7-segment LED displays 82 in a multiplexed fashion. Individual displays are selected sequentially through a column driver 84, and within each selected display the seven segments are controlled through segment drivers 86.

When the switch 22 on the housing is pressed, it closes the circuit from the battery 78 through resistors R5 and R6 and diode D1 to ground. The capacitor C1 is quickly charged, and field effect transistor T1 is turned on. Through transistor T1, the V+ potential from the storage cell 78 is applied to a voltage regulator 86. The regulator 86 provides the regulated +5 volts to the system. It also provides a reset signal to the microprocessor. The reset signal is low until the +5 volt reference is available and thus holds the microprocessor in a reset state. When the +5 volts is available, the reset signal goes high, and the microprocessor begins its programmed routine.

When the switch 22 is released, it opens its circuit, but a charge is maintained on capacitor C1 to keep transistor T1 on. Thus, the system continues to operate. However, the capacitor C1 and transistor T1 provide a very simple watchdog circuit. Periodically, the microprocessor applies a signal through driver 84 to the capacitor C1 to recharge the capacitor and thus keep the transistor T1 on. If the microprocessor should fail to continue its programmed routine, it fails to charge the capacitor C1 within a predetermined time during which the charge on C1 leaks to a level at which transistor T1 turns off. Thus, the microprocessor must continue in its programmed routine or the system shuts down. This prevents spurious readings when the processor is not operating properly.

With transistor T1 on, the switch 22 can be used as an input through diode D2 to the microprocessor to initiate any programmed action of the processor.

In addition to the display, the system has a sound output 90 which is driven through the driver 84 by the microprocessor.

In order to provide an analog output from the detector, a digital-to-analog convertor 92 is provided. When selected by line 94, the convertor converts serial data on line 96 to an analog output made available to a user.

Both calibration and characterization data required for processing by the microprocessor may be stored in an electrically erasable programmable read only memory (EEPROM) 100. The EEPROM may, for example, be a 93c46 sold by International CMOS Technologies, Inc. The data may be stored in the EEPROM by the microprocessor when the EEPROM is selected by line 102. Once stored in the EEPROM, the data is retained even after power down. Thus, though electrically programmable, once programmed the EEPROM serves as a virtually nonvolatile memory.

Prior to shipment, the EEPROM may be programmed through the microprocessor to store calibration data for calibrating the thermistor and thermopile. Further, characterization data which defines the personality of the infrared detector may be stored. For example, the same electronics hardware, including the microprocessor 73 and its internal program, may be used for a tympanic temperature detector in which the output is accurate in the target temperature range of about 60° F. to a 110° F. or it may be used as an industrial detector in which the target temperature range would be from about −100° F. to 5000° F. Further, different modes of operation may be programmed into the system. For example, several different uses of the sound source 90 are available.

Proper calibration of the detector is readily determined and the EEPROM is readily programmed by means of an optical communication link which includes a transistor T2 associated with the display. A communication boot may be placed over the end of the detector during a calibration/characterization procedure. A photodiode in the boot generates a digitally encoded optical signal which is filtered and applied to the detector T2 to provide an input to the microprocessor 73. In a reverse direction, the microprocessor, may communicate optically to a detector in the boot by flashing specific segments of the digital display 82. Through that communication link, an outside computer 106 can monitor the outputs from the thermistor and thermopile and perform a calibration of the devices. A unit to be calibrated is pointed at each of two black body radiation sources while the microprocessor 73 converts the signals and sends the values to the external computer. The computer is provided with the actual black body temperatures and ambient temperature in the controlled environment of the detector, computes calibration variables and returns those variable to be stored in the detector EEPROM. Similarly, data which characterizes a particular radiation detector may be communicated to the microprocessor for storage in the EEPROM.

A switch 108 is positioned behind a hole 110 (FIG. 1) in the radiation detector so that it may be actuated by a rigid metal wire or pin. Through that switch, the user may control some specific mode of operation such as converting the detector from degrees Fahrenheit to degrees centigrade. That mode of operation may be stored by the microprocessor 73 in the EEPROM so that the detector continues to operate in a specific mode until a change is indicated by closing the switch 108.

A switch 106 may be provided either internally or through the housing to the user to set a mode of operation of the detector. By positioning the switch at either the lock position, the scan position or a neutral position, any of three modes may be selected. The first mode is the normal scan mode where the display is updated continuously. A second mode is a lock mode where the display locks after a selectable delay and then remains frozen until power is cycled or, optionally, the power-on button is pushed. The sound source may be caused to sound at the time of lock. The third mode is the peak mode where the display reads the maximum value found since power-on until power is cycled or, optionally, the power-on button is pushed.

The processor determines when the voltage from the divider R1, R2 drops below each of two thresholds. Below the higher threshold, the processor periodically enables the sound source to indicate that the battery is low and should be replaced but allows continued readout from the display. Below the lower threshold, the processor determines that any output would be unreliable and no longer displays temperature readings. The unit would then shut down upon release of the power button.

In the present system, the target temperature is computed from the relationship $$T_T^4 = Kh(H - H_o) + T_H^4 \quad (1)$$

where $T_T$ is the target temperature, Kh is a gain calibration factor, H is the radiation sensor signal which is offset by $H_o$ such that $(H - H_o) = 0$ when the target is at the cold junction temperature of the device to counter any electronic offsets in the system, and $T_H$ is the hot junction temperature. This relationship differs from that previously used in that Kh is temperature compensated relative to the average temperature of the thermopile rather than the cold junction, or ambient, temperature. Further, the hot junction temperature rather than the cold junction temperature is referenced in the relationship.

The gain calibration factor Kh is temperature compensated by the relationship $$Kh = G\left(1 - Tco\left(\frac{T_H - T_C}{2} - Tz\right)\right) \quad (2)$$

where G is an empirically determined gain in the system, Tco is the temperature coefficient of the Seebeck coefficient of the thermopile and Tz is the temperature at which the instrument was calibrated. The use of the average temperature of the thermopile rather than the cold junction temperature provides for a much more accurate response where a target temperature is significantly different from the ambient temperature.

As noted, the relationship by which the target temperature is determined includes the hot junction temperature as the second term rather than the cold junction temperature. Hot junction temperature is computed from the relationship $$V_s = J\alpha_{tav}(T_H - T_C) \qquad (3)$$

where $J_N$ is the number of junctions in the thermopile and $\alpha_{tav}$ is the Seebeck coefficient at the average temperature of the thermopile. The Seebeck coefficient can be determined from the relationship $$\alpha_{tav} = \alpha_{ts}\left(1 - Tco\left(\frac{T_H - T_C}{2} - T_S\right)\right) \qquad (4)$$

where $\alpha_{ts}$ is the specified Seebeck coefficient at a particular specification temperature and $T_S$ is that specification temperature. Again, it can be seen that temperature compensation is based on the average thermopile temperature rather than just the cold junction temperature. By substituting equation (4) into equation (3) and solving for $T_H$, the hot junction temperature is found to be $$T_H = [(Tco*T_S+1) \pm [(Tco*Ts+1)^2 - (2*Tco)*[(Tco((Tc*Ts)-(Tc^2/2)) + Tc + (V_S/J*\alpha_{ts})]]^{\frac{1}{2}}]/Tco \qquad (5)$$

The actual sensor output $V_S$ can be determined from the digital value available to the processor from the equation:

$$V_S = (H - H_o)\frac{K_{AD}}{G_{FE}} \qquad (6)$$

where $K_{AD}$ is the analog-to-digital conversion factor in volts/bit and $G_{FE}$ is the gain of the front end amplifier.

Reference to the hot junction temperature rather than the cold junction temperature in each term of the relationship for determining the target temperature provides for much greater accuracy over a wide range of ambient temperatures and/or target temperatures.

To provide a temperature readout, the microprocessor makes the following computations: First the signal from thermistor RT1 is converted to temperature using a linear approximation. Temperature is defined by a set of linear equations $$y = M(x - xo) + b$$

where x is an input and xo is an input end point of a straight line approximation. The values of M, xo and b are stored in the EEPROM after calibration. Thus, to obtain a temperature reading from the thermistor, the microprocessor determines from the values of xo the line segment in which the temperature falls and then performs the computation for y based on the variables M and b stored in the EEPROM.

The hot junction temperature is computed. A fourth power representation of the hot junction temperature is then obtained by a lookup table in the processor ROM.

The sensed radiation may be corrected using the gain calibration factor Kh, the sensor gain temperature coefficient Tco, the average of the hot and cold junction temperatures and a calibration temperature Tz stored in the EEPROM. The corrected radiation signal and the fourth power of the hot junction temperature are summed, and the fourth root is taken. The fourth root calculation is also based on a linear approximation which is selected according to the temperature range of interest for a particular unit. Again, the break points and coefficients for each linear approximation are stored in the EEPROM and are selected as required.

An additional factor based on ambient temperature may also be included as an adjustment. The temperature of the ear $T_e$ is sensed instead of the temperature of the tympanic membrane, the temperature sensed by the thermopile is not actually the core temperature $T_{cr}$. There is thermal resistance between $T_{cr}$ and $T_e$. Further, there is thermal resistance between the sensed ear temperature and the ambient temperature. The result is a sense temperature $T_e$ which is a function of the core temperature of interest and the ambient temperature. Based on an assumed constant $K_C$ which is a measure of the ratio of thermal resistances between $T_{cr}$, $T_e$ and $T_a$, $T_{cr}$ and $T_a$ core temperature can be computed as $$T_{cr} = T_a + \frac{T_e - T_a}{k_c}$$

This computation can account for a difference of from one-half to one degree or more between core temperature and sensed ear temperature, depending on ambient temperature.

A similar compensation can be made in other applications. For example, in differential cutaneous temperature scanning, the significance of a given differential reading may be ambient temperature dependent.

The actual computations performed by the processor are as follows, where:

H is the digital value of radiation signal presented to the processor
$H_o$ is the electronic offset
Hc is corrected H (deg $K^4$)
Tc is ambient and cold junction temperature (deg F)
Taf is 4th power of Tamb (deg $K^4$)
Tt is target temperature (deg F)
Tz is ambient temp during cal (deg F)
Td is the displayed temperature
Rt is the thermistor signal
Kh is a radiation sensor gain cal factor
Zt is a thermistor zero cal factor
Th is the hot junction temperature
$\alpha_{ts}$ is the Seebeck coefficient of the thermopile at a specified temperature
J is the number of junctions in the thermopile
Tco is a temperature coefficient for the Seebeck coefficient
Ts is the temperature at which $\alpha_{ts}$ is specified
Tcr is core temperature
kc is a constant for computing core temperature
$V_S$ is the sensor output voltage
$G_{FE}$ is the gain of the front end amplifier
$K_{AD}$ is the analog-to-digital conversion factor
$V_S = (H - H_o)K_{AD}/G_{FE}$
Tc(deg F) = Thermistor lookup table (Rt) − Zt
$T_H = [(Tco*T_S+1) \pm [(Tco*Ts+1)^2 - (2*Tco)*[(Tco((Tc*Ts)-(Tc^2/2)) + Tc + (V_S/J*\alpha_{ts})]]^{\frac{1}{2}}]/Tco$
Hc(deg $K^4$) = Kh*(H−$H_o$)*(1+Tco*((Th−Tc)/2−Tz))
Thf(deg $K^4$) = 4th power lookup table (Tc)
Tt(deg F) = (Hc+Thf)$^{\frac{1}{4}}$ (Final lookup table)
Tcr = Te+(Tt−Te)/kc
Tt(deg C) = (5/9)*(Tf(deg F)−32) optional The following is a list of the information which may be contained in the EEPROM and therefore be programmable at the time of calibration:

Radiation sensor offset
Radiation sensor gain
Radiation sensor temperature coefficient
Thermistor offset
Ambient temperature at calibration
Thermistor lookup table
Final temperature lookup table
Adjustment factor F
Sound source functions:
  Beep at button push in lock mode
    none/20/40/80 milliseconds long
  Beep at lock
    none/20/40/80 milliseconds long
  Beep at power down
    none/20/40/80 milliseconds long
  Beep at lowbattery
    none/20/40/80 milliseconds long
    interval 1/2/3 sec
    single/double beep
Timeout functions:
  Time to power-down
    0.5 to 128 sec in 0.5 sec increments
  Delay until lock
    0.5 to 128 sec in 0.5 sec increments
Other functions:
  Power-on button resets lock cycle
  Power-on button resets peak detect
  Display degrees C./degrees F.
  EEPROM "Calibrated" pattern to indicate that the device has been calibrated
  EEPROM checksum for a self-check by the processor FIGS. 9A-9D provide a flowchart of the firmware stored in the microprocessor 73. From reset when the instrument is turned on, the system is initialized at 110 and the contents of the EEPROM are read into memory in the microprocessor at 112. At 114, the processor reads the state of power and mode switches in the system. At 116, the system determines whether a mode switch 113 has placed the system in a self-test mode. If not, all eights are displayed on the four-digit display 82 for a brief time. At 120, the system performs all A-to-D conversions to obtain digital representations of the thermopile output and the potentiometer settings through multiplexor 76.

The system then enters a loop in which outputs dictated by the mode switch are maintained. First the timers are updated at 122 and the switches are again read at 124. When the power is switched off, from 126 the system enters a power down loop at 128 until the system is fully down. At 130, the mode switch is checked and if changed the system is reset. Although not in the tympanic temperature detector, some detectors have a mode switch available to the user so that the mode of operation can be changed within a loop.

At 132, 136 and 140, the system determines its mode of operation and enters the appropriate scan process 134, lock process 138 or peak process 142. In a scan process, the system updates the output to the current reading in each loop. In a lock process, the system updates the output but locks onto an output after some period of time. In the peak process, the system output is the highest indication noted during a scan. In each of these processes, the system may respond to the programming from the EEPROM to perform any number of functions as discussed above. In the peak process which is selected for the tympanic temperature measurement, the system locks onto a peak measurement after a preset period of time. During assembly, the system may be set at a test mode 144 which will be described with respect to FIG. 9D.

In any of the above-mentioned modes, an output is calculated at 146. Then the system loops back to step 122. The calculation 146 is illustrated in FIG. 9B.

Figure 9A:
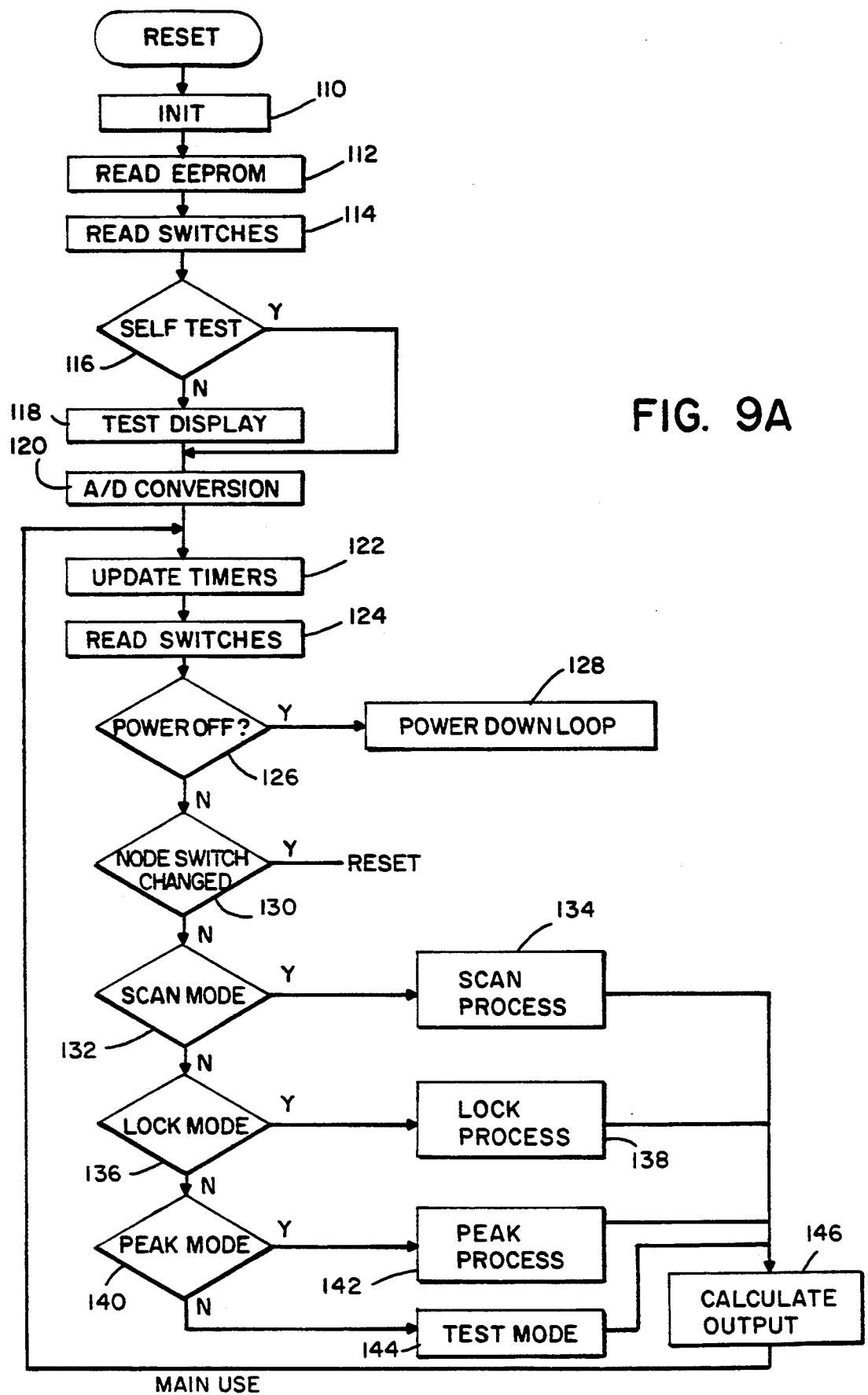
FIGS. 9A–9D are flow charts of the system firmware.
Figure 9B:
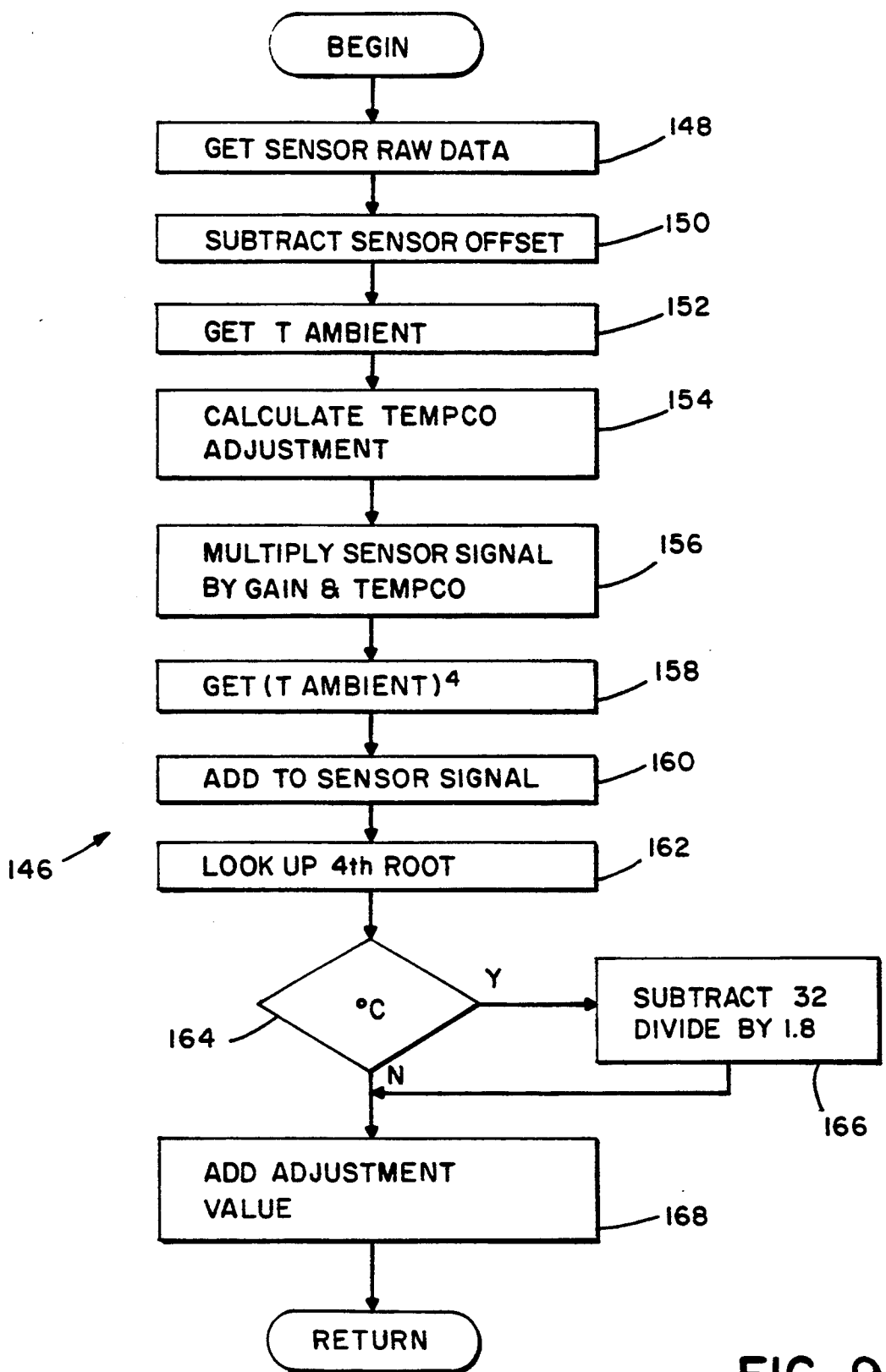

At 148 in FIG. 9B, the raw sensor data is obtained from memory. The sensor offset taken from the EEPROM is subtracted at 150, and the ambient temperature previously obtained from the potentiometer RT1 is accessed at 152. The temperature coefficient adjustment is calculated at 154. At 156, the sensed signal is multiplied by the gain from EEPROM and by the temperature coefficient. At 158, the fourth power of the ambient temperature is obtained, and at 160 it is added to the sensor signal. At 162, the fourth root of the sum is obtained through a lookup table. Whether the display is in degrees centigrade or degrees Fahrenheit is determined at 164. If in degrees centrigrade, a conversion is performed at 166. At 168, adjustment values, including that from the potentiometer R4, are added.

Figure 9C:
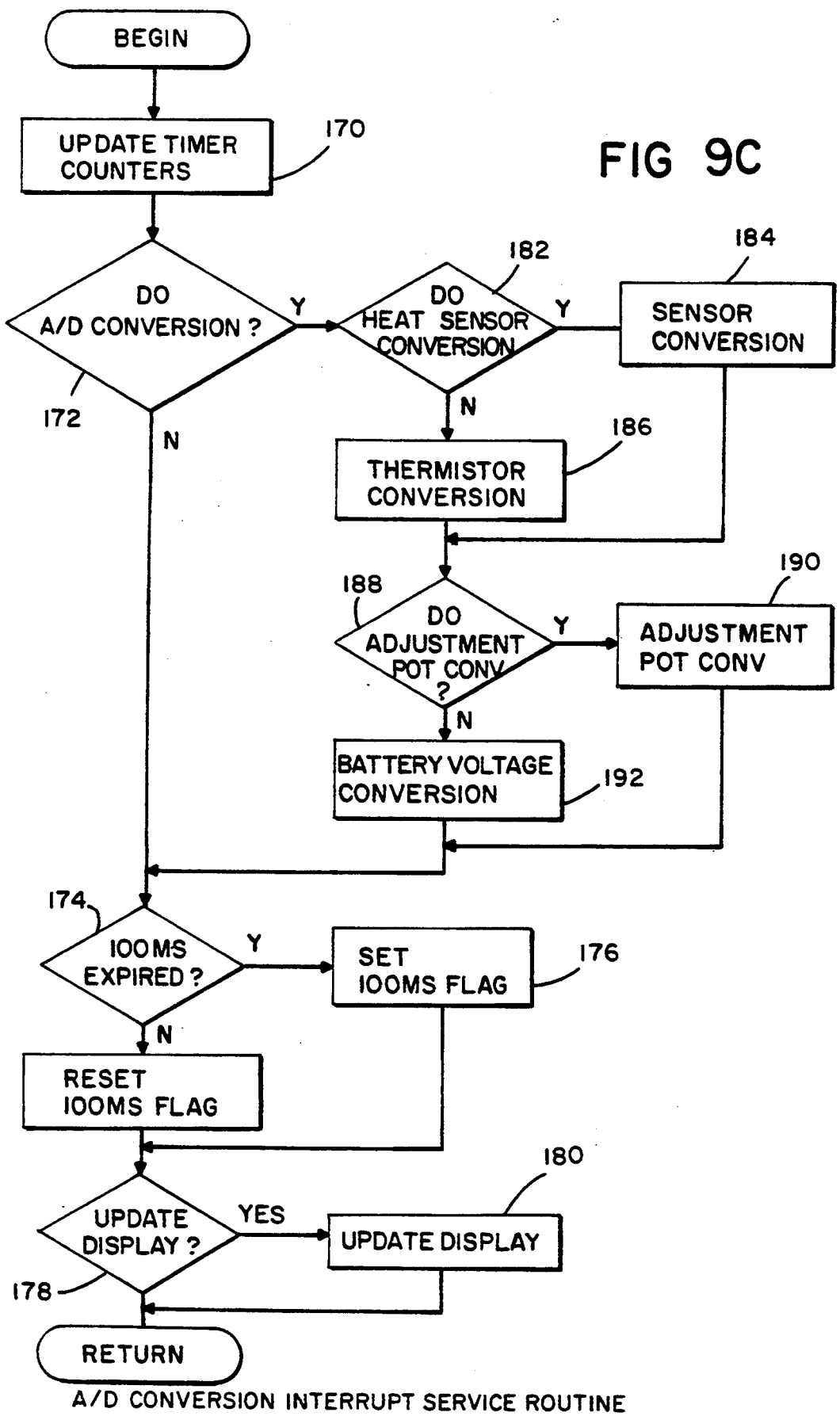

Analog-to-Digital conversion is performed periodically during an interrupt to the loop of FIG. 9A which occurs every two milliseconds. The interrupt routine is illustrated in FIG. 9C. Timer counters are updated at 170. A-to-D conversions are made from 172 only every 100 milliseconds when a flag has been set in the prior interrupt cycle. During most interrupts, an A/D conversion does not occur. Then, the 100-millisecond counter is checked at 174, and if the count has expired, a flag is set at 176 for the next interrupt. The flag is checked at 178 and, if found, the display is updated at 180. The system then returns to the main loop of FIG. 9A.

Where the 100 millisecond flag is noted at 172, an A-to-D conversion is to be performed. The system first determines at 182 whether a count indicates there should be a conversion of the thermopile output at 184 or a conversion of the the thermistor output at 186. The thermopile sensor conversion is performed nine out of ten cycles through the conversion loop. At 188, the system checks to determine whether a conversion is made from the potentiometer R4 or from the battery voltage divider R1, R2 at 192. These conversions are made alternately.

Figure 9D:
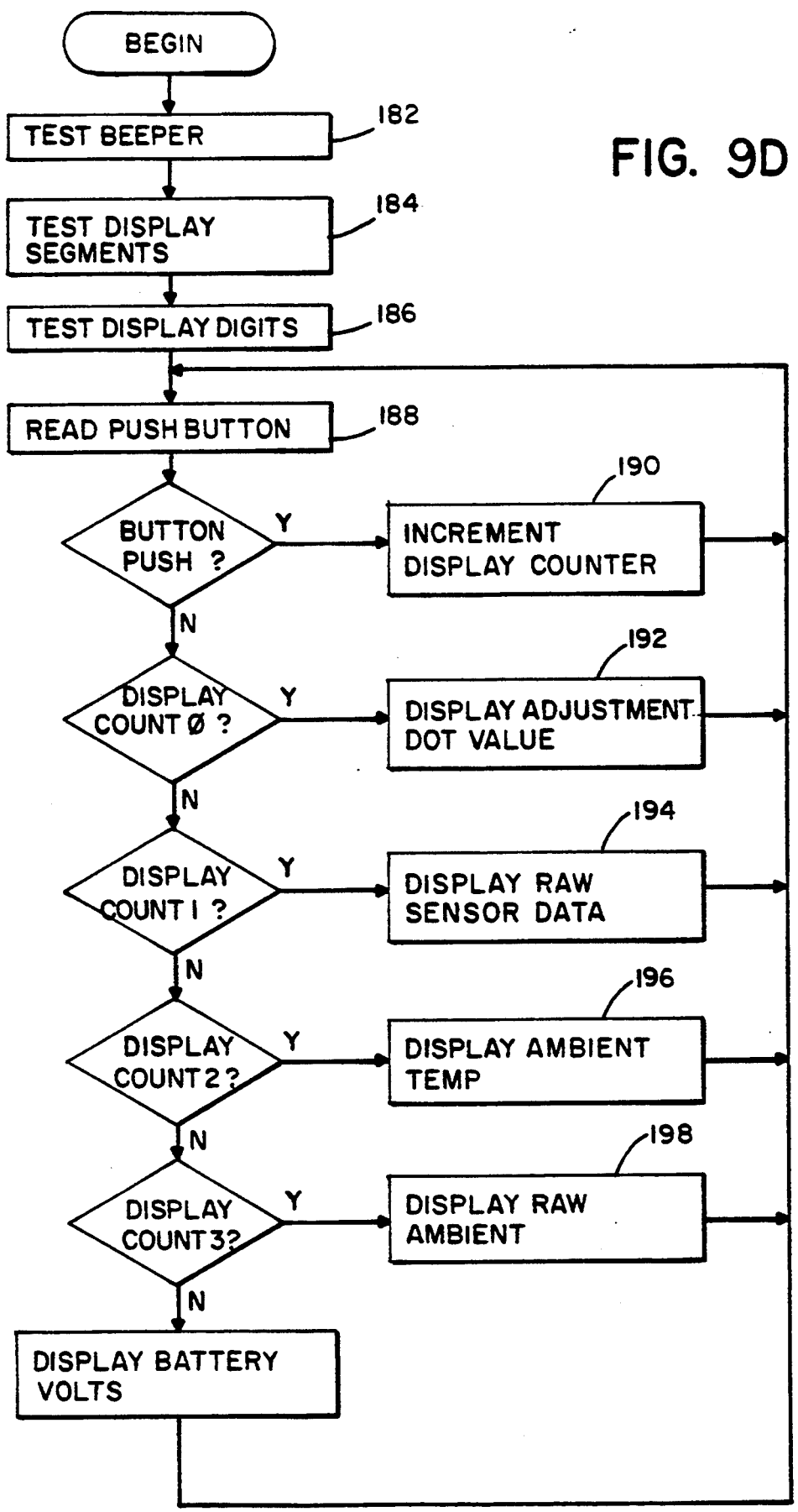

FIG. 9D illustrates the self-test sequence which is called by the mode switch 113 only during assembly. During the test, the beeper sounds at 182 and all display segments are displayed at 184. Then the system steps each character of the display from zero through nine at 186. The system then enters a test loop. At 188, the system senses whether the button 108 has been pressed. If so, a display counter is incremented at 190. The display for the unit then depends on the count of the display counter. With the zero count, the adjustment potentiometer value is displayed at 192. Thereafter, if the display counter is incremented by pressing the button 108, the raw sensor data is displayed. With the next increment, ambient temperature is displayed at 196, and with the next increment, the raw output from the ambient temperature sensor RT1 is displayed. With the next increment, the battery voltage is displayed. After the test, the assembler sets the mode switch to the proper operating mode.

While this invention has been particularly shown and described with references to preferred embodiments thereof, it will be understood by those skilled in the art that various changes in form and details may be made therein without departing from the spirit and scope of the invention as defined by the appended claims. For example, most features of the invention may be applied to a device having a pyroelectric radiation sensor. Also certain features such as the low reflectance, high thermal conductivity tube may provide stable response and narrow field of view even where the tube is thermally isolated from the sensor. In that case, a second temperature sensor would be provided for the tube to compensate for temperature differences between the tube and sensor cold junction.

I claim:

1. A radiation detector comprising:
   an infrared radiation sensor positioned in a low thermal conductivity environment; and
   an elongated thermally conductive tube extending from a distal end to be directed toward a target to a rear volume of larger cross-sectional area than the tube, in which the sensor is mounted, the tube providing a field of view from the sensor of about sixty degrees or less, the tube and the walls of the rear volume being of high thermal conductivity and thermally coupled to the radiation sensor.

2. A radiation detector as claimed in claim 1 wherein the tube comprises a non-reflective inner surface for preventing radiation incapable of passing directly through the tube from being provided to the sensor.

3. A radiation detector as claimed in claim 2 wherein the tube provides a narrow field of view of about thirty degrees or less.

4. A radiation detector as claimed in claim 2 wherein the non-reflective inner surface of the tube is formed of metal oxide.

5. A tympanic temperature detector as claimed in claim 2 further comprising a window mounted adjacent to an end of the tube.

6. A radiation detector as claimed in claim 1 further comprising an extension surrounding the tube and having a distal end adapted to be inserted into an ear canal.

7. A radiation detector as claimed in claim 6 wherein the extension has an increasing diameter along its length from its distal end forming a substantially conical shape.

8. A radiation detector as claimed in claim 7 wherein the conical shape further includes an included angle of about 25-60 degrees.

9. A radiation detector as claimed in claim 7 wherein the extension has a diameter of less than about 7 mm along a portion of its length extending from its distal end such that the extension is adapted to be inserted into a normal ear canal.

10. A radiation detector as claimed in claim 7 wherein the extension has a diameter of about 3-6 mm along a portion of its length extending from its distal end such that the extension is adapted to be inserted into a small ear canal.

11. A radiation detector as claimed in claim 6 wherein the extension has a substantially constant diameter along a first portion of its length from its distal end and an increasing diameter along a second portion of its length extending from the first portion.

12. A radiation detector as claimed in claim 1 wherein the tube comprises a reflective inner surface.

13. A radiation detector as claimed in claim 12 further comprising a window mounted adjacent to the distal end of the tube.

14. A radiation detector as claimed in claim 13 wherein the window is a lens.

15. A radiation detector as claimed in claim 1 wherein the length of the tube and the field of view through the radiation tube from the sensor are such that the sensor only views an ear canal within less than about 1 centimeter of a tympanic membrane.

16. A radiation detector as claimed in claim 1 wherein the length of the tube and the field of view through the tube from the sensor are such that the sensor only views substantially the tympanic membrane.

17. A radiation detector as claimed in claim 1 wherein the sensor is a thermopile and the inner RC time constant is for the response of a cold junction of the thermopile.

18. A radiation detector as claimed in claim 17 wherein an outer thermal RC time constant for thermal conduction through a thermal barrier to the tube is at least two orders of magnitude greater than an inner thermal RC time constant for the thermopile junction to heat transferred to the tube through the thermal barrier.

19. A tympanic temperature detector as claimed in claim 1 further comprising a rigid structure of high thermal conductivity material positioned in the rear volume and thermally coupled to the tube and a window mounted on the rigid structure and thermally coupled thereto, wherein the sensor is mounted across an opening in the rigid structure and receives radiation through the window.

20. A radiation detector as claimed in claim 14 wherein rigid structure is beryllium oxide.

21. A radiation detector comprising:
    a thermopile sensor and;
    a thermal mass enclosing the sensor in a low conductivity environment the thermal mass being formed of unitary structure of high thermal conductivity material, the unitary thermal structure comprising an elongated high thermal conductivity tube of a first internal diameter extending from the distal end to a rear volume of larger internal diameter in which the sensor is mounted, the unitary thermal structure having an outer surface with an outer diameter at its distal end which is less than an outer diameter about the rear volume, the outer surface being tapered about the tube such that a unitary thermal mass of increasing outer diameter is provided about the end of the tube adjacent to the rear volume.

22. A radiation detector as claimed in claim 21 further comprising an additional thermal mass surrounding the rear volume and a portion of the tube and thermally coupled to the unitary thermal structure.

23. A tympanic temperature detector as claimed in claim 21 wherein the tube provides a narrow field of view from the thermopile of about sixty degrees or less.

24. A tympanic temperature detector as claimed in claim 21 further comprising a window mounted to the unitary thermal structure adjacent to an end of the tube.

25. A tympanic temperature detector as claimed in claim 21 wherein the length of the tube and the field of view through the tube from the thermopile are such that the sensor only views an ear canal within less than about 1 centimeter of a tympanic membrane.

26. A tympanic temperature detector as claimed in claim 21 further comprising a rigid structure of high thermal conductivity material positioned in the rear volume and thermally coupled to the unitary thermal structure, a window mounted on the rigid structure and thermally coupled thereto and the thermopile is being mounted across an opening in the rigid structure and receives radiation through the window.

27. A tympanic temperature detector as claimed in claim 26 wherein the rigid structure is comprised substantially of beryllium oxide.

28. A radiation detector comprising:
an infrared radiation sensor for receiving radiation from an external target; and
a thermally conductive tube passing radiation from the external target to the sensor, the tube having a non-reflective inner surface for substantially preventing radiation incapable of passing directly through the tube from being provided to the sensor.

29. A radiation detector as claimed in claim 28 wherein the sensor is a thermopile.

30. A radiation detector as claimed in claim 28 wherein the tube provides a narrow field of view from the sensor of about thirty degrees or less.

31. A method of obtaining ear temperature comprising:
providing a radiation detector comprising an extension having an infrared radiation sensor for receiving radiation from an external target and a thermally conductive tube for passing radiation from the external target to the sensor, the detector further comprising electronics for detecting the peak radiation sensed by the sensor;
inserting the extension into an ear;
pivoting the extension to scan the ear canal, the sensor sensing radiation during scanning; and
detecting the peak radiation to obtain an ear temperature in the electronics.

32. A method as claimed in claim 31 wherein the extension is adapted to be inserted into an ear canal.

33. A method as claimed in claim 31 wherein the sensor senses a narrow field of view of sixty degrees or less.

34. A method as claimed in claim 31 wherein the sensor senses a narrow filed of view of about thirty degrees or less and the extension has a substantially conical shape along a portion of its length from its distal end.

35. A method as claimed in claim 34 wherein the extension has a diameter of about 3-6 mm along a portion of its length from its distal end, the conical shape of the extension further including an included angle of about 25-60 degrees.

36. A method as claimed in claim 35 wherein the extension is inserted into an ear canal up to about one-third of the length of the ear canal.

37. A radiation detector comprising an infrared radiation sensor mounted within a can and a tube of lesser internal diameter than the can and integral with the can, the tube having a gas tight window at a distal end thereof through which radiation passes to the sensor, a gaseous environment being maintained about the sensor within the can and through the length of the tube.

38. A radiation detector as claimed in claim 37 wherein the interior of the can is open to the interior of the tube.

39. A radiation detector comprising:
an infrared radiation sensor positioned in a low thermal conductivity environment; and
an elongated thermally conductive tube extending from a distal end to be directed toward a target to a rear volume in which the sensor is mounted, the tube providing a field of view from the sensor of about sixty degrees or less;
wherein an outer thermal RC time constant for thermal conduction through a thermal barrier to the tube is at least two orders of magnitude greater than an inner thermal RC time constant for the temperature response of a radiation sensor reference junction to heat transferred to the tube through the thermal barrier.

40. A radiation detector as claimed in claim 39 wherein the radiation sensor is a thermopile.

41. A radiation detector comprising;
an infrared radiation sensor; and
a unitary structure of high thermal conductivity material enclosing the sensor in a low conductivity environment and in close thermal contact with the sensor, the unitary thermal structure comprising a tube of a first internal diameter extending from an opening to a rear volume of larger internal diameter in which the sensor is mounted, the unitary thermal structure having an outer surface with an outer diameter at its end adjacent to the opening which is less than an outer diameter about the rear volume, the outer surface of the unitary thermal structure being tapered about the tube such that a unitary thermal mass of increasing outer diameter is provided about the tube.

42. A radiation detector as claimed in claim 41 further comprising an additional thermal mass surrounding the rear volume and a portion of the unitary thermal mass and in close thermal contact with the unitary thermal structure.

43. A radiation detector as claimed in claim 41 wherein the tube provides a narrow filed of view from the sensor of about sixty degrees or less.

44. A radiation detector as claimed in claim 41 further comprising a window of transparent material mounted to the unitary thermal structure adjacent to an end of the tube.

45. A radiation detector as claimed in claim 41 wherein the length of the tube and the field of view through from the sensor are such that the sensor only views an ear canal within less than about 1.0 centimeter of a tympanic membrane.

46. A tympanic temperature detector comprising:
a radiation sensor;
a can enclosing the radiation sensor in a low conductivity environment, the can comprising a tube extended from an opening to a rear volume in which the radiation sensor is mounted, the tube providing a field of view from the radiation sensor of about sixty degrees or less; and
wherein an outer thermal RC time constant for thermal conduction through a thermal barrier to the can is at least two orders of magnitude greater than an inner thermal RC time constant for the temperature response of a radiation sensor reference junction to heat transferred to the can through the thermal barrier.

47. A temperature sensor as claimed in claim 46 further comprising a window of transparent material mounted to the unitary thermal structure adjacent an end of the tube.

48. A tympanic temperature sensor as claimed in claim 46 wherein the length of the tube and the field of view through the tube from the sensor are such that the thermopile only views an ear canal within about 1.5 centimeters of a tympanic membrane.

49. A tympanic temperature sensor as claimed in claim 46 wherein the length of the radiation guide and the field of view through the tube from the thermopile are such that the thermopile only views an ear canal within about 1.0 centimeter of a tympanic membrane.

* * * * *

UNITED STATES PATENT AND TRADEMARK OFFICE
CERTIFICATE OF CORRECTION

PATENT NO. : 5,445,158
DATED : August 29, 1995
INVENTOR(S) : Francesco Pompei

It is certified that error appears in the above-indentified patent and that said Letters Patent is hereby corrected as shown below:

On the front page, delete "[*] Notice: The portion of the term of this patent subsequent to Feb. 19, 2008 has been disclaimed."

In claim 5, column 21, line 40, change "claim 2" to --claim 1--.

In claim 20, column 22, line 33, change "claim 14" to --claim 19--

In claim 34, column 23, line 44, change "filed" to --field--.

In claim 43, column 24, line 37, change "filed" to --field--.

Signed and Sealed this

Twenty-eighth Day of November 1995

BRUCE LEHMAN

Attest:

Attesting Officer

Commissioner of Patents and Trademarks